(12) United States Patent
Coleman et al.

(10) Patent No.: US 9,301,761 B2
(45) Date of Patent: Apr. 5, 2016

(54) ANASTOMOSIS DEVICES AND METHODS

(76) Inventors: James E. Coleman, Terenure (IE); Christy Cummins, Naas (IE)

( * ) Notice: Subject to any disclaimer, the term of this patent is extended or adjusted under 35 U.S.C. 154(b) by 674 days.

(21) Appl. No.: 11/876,131

(22) Filed: Oct. 22, 2007

(65) Prior Publication Data

US 2009/0105733 A1 Apr. 23, 2009

(51) Int. Cl.
*A61B 17/08* (2006.01)
*A61B 17/11* (2006.01)
*A61B 17/12* (2006.01)
*A61F 2/06* (2013.01)
*A61F 2/07* (2013.01)
*A61B 17/00* (2006.01)
*A61F 2/89* (2013.01)

(52) U.S. Cl.
CPC .......... *A61B 17/11* (2013.01); *A61B 17/12031* (2013.01); *A61B 17/12036* (2013.01); *A61B 17/12118* (2013.01); *A61B 17/12131* (2013.01); *A61B 17/12159* (2013.01); *A61F 2/064* (2013.01); *A61F 2/07* (2013.01); *A61B 17/1114* (2013.01); *A61B 2017/00986* (2013.01); *A61B 2017/1103* (2013.01); *A61B 2017/1107* (2013.01); *A61B 2017/1135* (2013.01); *A61B 2017/12054* (2013.01); *A61F 2/89* (2013.01); *A61F 2002/061* (2013.01); *A61F 2002/065* (2013.01); *A61F 2220/0058* (2013.01); *A61F 2250/0007* (2013.01)

(58) Field of Classification Search
CPC ............. A61B 17/11; A61B 17/12036; A61B 17/12131; A61B 17/12118; A61B 17/12159; A61B 2017/12054; A61B 2017/1103; A61B 2017/1135; A61B 2017/00986; A61B 2017/1107; A61B 17/1114; A61F 2/064; A61F 2/07; A61F 2002/065; A61F 2002/061; A61F 2/89; A61F 2250/0007; A61F 2220/0058

USPC .................................. 606/153, 151, 155, 213
See application file for complete search history.

(56) References Cited

U.S. PATENT DOCUMENTS 3,942,407 A 3/1976 Mortensen
4,467,804 A 8/1984 Hardy et al.
(Continued)

FOREIGN PATENT DOCUMENTS

EP 1908419 A1 4/2008
WO 0009040 A1 2/2000
(Continued)

OTHER PUBLICATIONS

Examination Communication from European Patent Office dated Apr. 20, 2009 (EU07703241.5).
(Continued)

*Primary Examiner* — Jing Ou
(74) *Attorney, Agent, or Firm* — Mintz Levin Cohn Ferris Glovsky and Popeo, P.C.

(57) ABSTRACT

Methods and devices are provided for anastomosing tissue in the body. In one exemplary embodiment, an anastomotic device is provided having an elongate tubular body that is disposable through a body lumen and that includes proximal and distal portions. The proximal and distal portions can each include a plurality of asymmetrical s-shaped slits and can each be adapted to expand upon rotation to form proximal and distal wings. The proximal and distal wings can extend toward one another to engage tissue therebetween and thereby form a passageway through the tissue.

15 Claims, 21 Drawing Sheets

(56) References Cited

U.S. PATENT DOCUMENTS

| | | |
|---|---|---|
| 4,766,898 A | 8/1988 | Hardy et al. |
| 5,035,702 A | 7/1991 | Taheri |
| 5,197,971 A | 3/1993 | Bonutti |
| 5,222,963 A | 6/1993 | Brinkerhoff et al. |
| 5,342,393 A | 8/1994 | Stack |
| 5,496,332 A | 3/1996 | Sierra et al. |
| 5,741,297 A | 4/1998 | Simon |
| 5,853,422 A | 12/1998 | Huebsch et al. |
| 6,024,756 A | 2/2000 | Huebsch et al. |
| 6,117,159 A | 9/2000 | Huebsch et al. |
| 6,183,496 B1 | 2/2001 | Urbanski |
| 6,190,353 B1 | 2/2001 | Makower et al. |
| 6,261,309 B1 | 7/2001 | Urbanski |
| 6,312,446 B1 | 11/2001 | Huebsch et al. |
| 6,355,052 B1 | 3/2002 | Neuss et al. |
| 6,375,671 B1 | 4/2002 | Kobayashi et al. |
| 6,461,320 B1 * | 10/2002 | Yencho et al. ............ 604/8 |
| 6,616,685 B2 | 9/2003 | Rousseau |
| 6,623,508 B2 | 9/2003 | Shaw et al. |
| 6,632,237 B2 | 10/2003 | Ben-David et al. |
| 6,666,873 B1 | 12/2003 | Cassell |
| 6,776,785 B1 | 8/2004 | Yencho et al. |
| 6,942,674 B2 | 9/2005 | Belef et al. |
| 6,960,224 B2 | 11/2005 | Marino et al. |
| 6,994,713 B2 | 2/2006 | Berg et al. |
| 7,018,388 B2 | 3/2006 | Yencho et al. |
| 7,022,127 B2 | 4/2006 | Suyker et al. |
| 7,108,702 B2 | 9/2006 | Yencho et al. |
| 7,149,587 B2 | 12/2006 | Wardle et al. |
| 7,608,086 B2 | 10/2009 | Tanaka et al. |
| 7,625,392 B2 | 12/2009 | Coleman et al. |
| 7,798,992 B2 | 9/2010 | Ortiz |
| 7,803,195 B2 | 9/2010 | Levy et al. |
| 7,833,280 B2 | 11/2010 | Stack et al. |
| 7,846,174 B2 | 12/2010 | Baker et al. |
| 7,892,214 B2 | 2/2011 | Kagan et al. |
| 8,109,946 B2 | 2/2012 | Cahill et al. |
| 8,157,833 B2 | 4/2012 | Au et al. |
| 8,192,457 B2 | 6/2012 | Coleman et al. |
| 8,197,498 B2 | 6/2012 | Coleman et al. |
| 8,366,742 B2 | 2/2013 | Coleman et al. |
| 2002/0026137 A1 | 2/2002 | Yencho et al. |
| 2002/0183768 A1 | 12/2002 | Deem et al. |
| 2003/0158578 A1 | 8/2003 | Pantages et al. |
| 2003/0171774 A1 | 9/2003 | Freudenthal et al. |
| 2004/0116992 A1 * | 6/2004 | Wardle et al. ............ 607/116 |
| 2004/0122456 A1 | 6/2004 | Saadat et al. |
| 2004/0243155 A1 | 12/2004 | Yencho et al. |
| 2005/0043759 A1 | 2/2005 | Chanduszko |
| 2005/0055050 A1 | 3/2005 | Alfaro |
| 2005/0070935 A1 * | 3/2005 | Ortiz ............ 606/153 |
| 2005/0075665 A1 | 4/2005 | Brenzel et al. |
| 2005/0149071 A1 | 7/2005 | Abbott et al. |
| 2005/0251209 A1 | 11/2005 | Saadat et al. |
| 2005/0267524 A1 | 12/2005 | Chanduszko |
| 2005/0273124 A1 | 12/2005 | Chanduszko |
| 2005/0273135 A1 | 12/2005 | Chanduszko et al. |
| 2005/0277966 A1 * | 12/2005 | Ewers et al. ............ 606/153 |
| 2005/0288786 A1 | 12/2005 | Chanduszko |
| 2006/0047308 A1 | 3/2006 | Ortiz et al. |
| 2006/0190036 A1 | 8/2006 | Wendel et al. |
| 2006/0196137 A1 | 9/2006 | Brenzel et al. |
| 2006/0211999 A1 * | 9/2006 | Fangrow ............ 604/246 |
| 2006/0217748 A1 | 9/2006 | Ortiz |
| 2006/0265004 A1 | 11/2006 | Callaghan et al. |
| 2007/0021758 A1 | 1/2007 | Ortiz |
| 2007/0066863 A1 | 3/2007 | Rafiee et al. |
| 2007/0106319 A1 | 5/2007 | Au et al. |
| 2007/0129755 A1 | 6/2007 | Abbott et al. |
| 2007/0185529 A1 | 8/2007 | Coleman et al. |
| 2007/0233162 A1 | 10/2007 | Gannoe et al. |
| 2008/0071376 A1 | 3/2008 | Kohm et al. |
| 2008/0147101 A1 | 6/2008 | Ortiz et al. |
| 2008/0221596 A1 * | 9/2008 | Thompson et al. ............ 606/153 |
| 2009/0088795 A1 | 4/2009 | Cahill |
| 2010/0004681 A1 | 1/2010 | Coleman et al. |
| 2010/0114128 A1 | 5/2010 | Coleman et al. |
| 2010/0256673 A1 | 10/2010 | Coleman et al. |
| 2012/0245625 A1 | 9/2012 | Coleman et al. |
| 2012/0265224 A1 | 10/2012 | Coleman et al. |
| 2013/0131719 A1 | 5/2013 | Coleman et al. |
| 2013/0165963 A1 | 6/2013 | Coleman et al. |

FOREIGN PATENT DOCUMENTS

| | | |
|---|---|---|
| WO | 0149185 | 7/2001 |
| WO | 0205718 A2 | 1/2002 |
| WO | WO-03034927 A1 | 5/2003 |
| WO | 2007013070 A1 | 2/2007 |
| WO | 2007073566 A1 | 6/2007 |
| WO | 2008040577 A1 | 4/2008 |

OTHER PUBLICATIONS

U.S. Appl. No. 12/266,174, filed Nov. 6, 2008.
Office Action dated Dec. 16, 2008 issued for U.S. Appl. No. 11/307,372.
Office Action dated Apr. 29, 2009 issued for U.S. Appl. No. 11/307,372.
International Application No. PCTEP2008008178 Search Report dated Jun. 8, 2009, 23 pgs.
Office Action dated Jul. 8, 2009 issued for U.S. Appl. No. 11/307,372.
Form PCT/ISA/206 for Application No. PCT/EP2008/008178 dated Mar. 10, 2009, 6 pgs.
International Preliminary Report on Patentability and Written Opinion of the ISA dated Apr. 27, 2010, 13 pgs.
International Search Report and Written Opinion mailed May 28, 2013 for Application No. PCT/EP12/076029 (16 Pages).

* cited by examiner

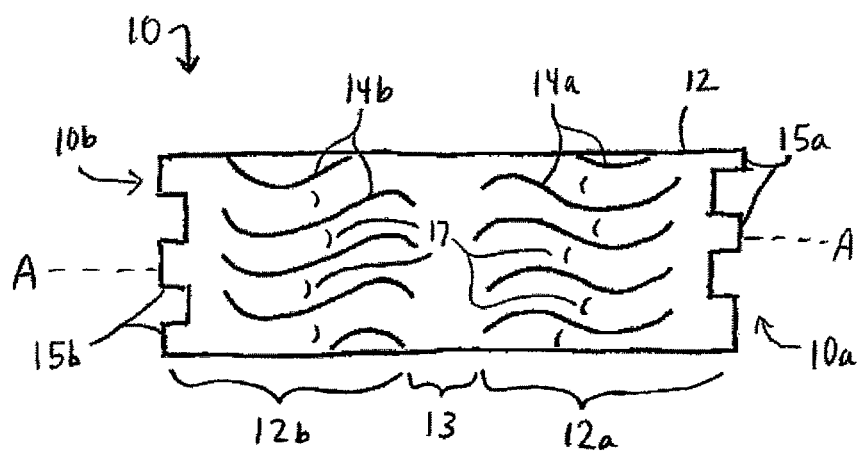
FIG. 1
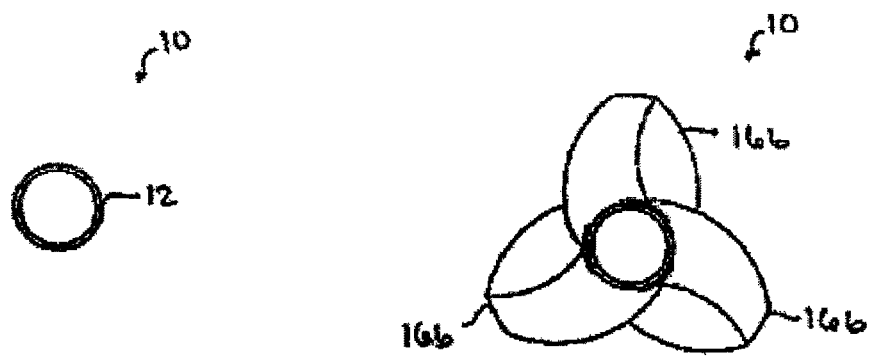
FIG. 2
FIG. 3

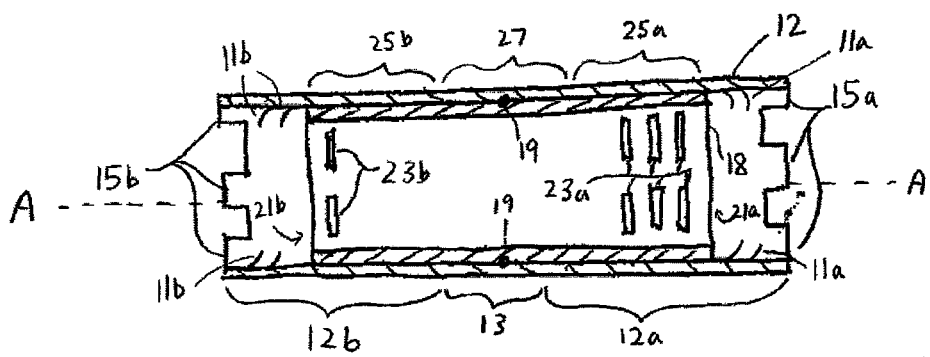
FIG.4
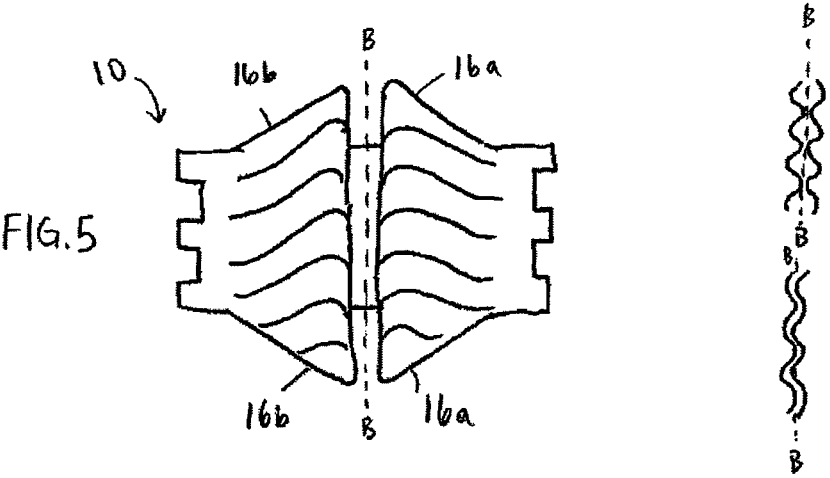
FIG.5
FIG.6
FIG.7
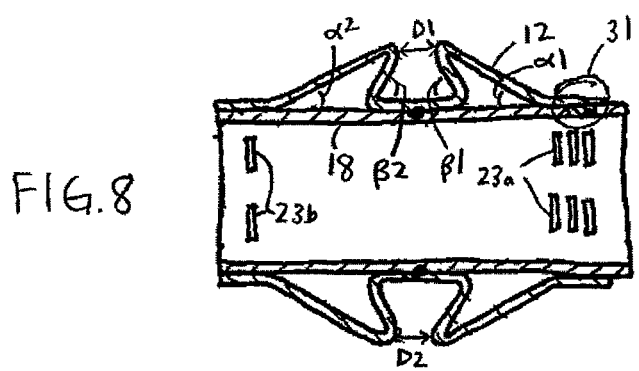
FIG.8

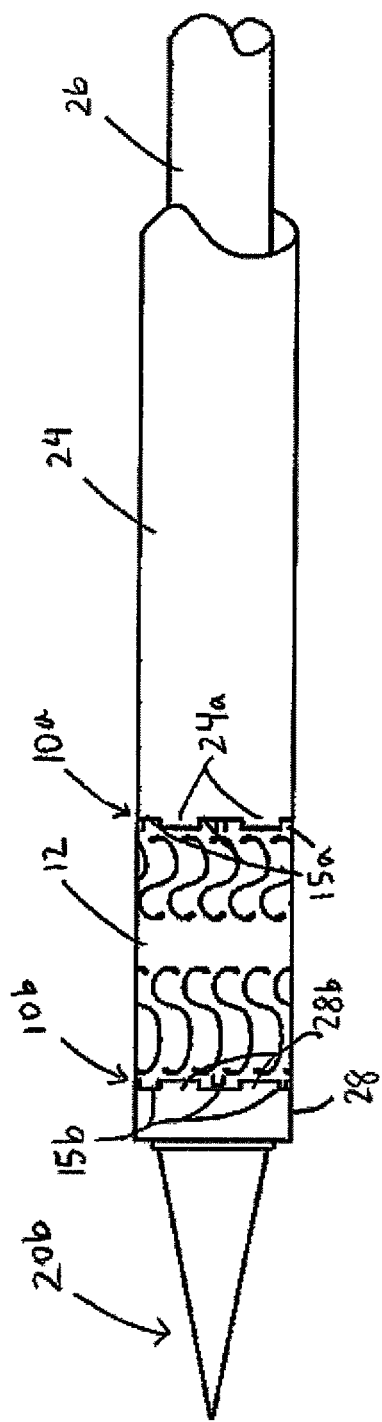

ANASTOMOSIS DEVICES AND METHODS

FIELD OF THE INVENTION

The present invention relates to methods and devices for forming an anatomosis between two body lumens.

BACKGROUND

Procedures to correct or relieve blocked or diseased luminal viscera of the body such as the bowel, bile duct, fallopian tube, ureter, and blood vessels generally involve moving or bypassing the blocked or diseased segment and performing a surgical anastomosis. Typically, a portion of a blocked or restricted luminal viscous, or a lesion or tumor on the viscous wall, is removed, thereby forming a break in the lumen. The break may then repaired by rejoining the two healthy luminal portions such as by suturing, stapling, or clamping the severed ends together.

Various apparatus have been suggested for anastomosing body lumens. One apparatus is a surgical anastomotic circular stapler. Generally, these staplers are inserted into and used to connect severed lumens with a circular ring of staples displayed around a circumference to connect the tissue. With this type of stapler, the tissue has to be intricately aligned along 360° of its cut surfaces before stapling so that no gaps exist between the connected tissue. Another apparatus is an anastomotic button made of metal or bioabsorbable material. These anastomotic devices receive open ends of two tubular body organs to be anastomosed over a pair of ring members. The ring members have annular connectors which can mate with each other to clamp the tubular body organs contiguous to each other so that they can grow and heal together. Such buttons, however, can be bulky, awkward, and difficult to use and position properly, particularly when used in tight quarters such as during laparoscopic procedures.

Accordingly, improved methods and devices for forming an anatomosis between two body lumens are needed.

SUMMARY

The present invention generally provides methods and devices for joining body lumens. In one embodiment, an anastomotic device is provided having an elongate tubular body that is disposable through a body lumen and that includes proximal and distal portions. The elongate tubular body can be formed from various materials, but in an exemplary embodiment it is formed from at least one of a deformable and a resorbable material. The proximal and distal portions can each include a plurality of asymmetrical s-shaped slits formed therein and adapted to expand upon rotation to form proximal and distal wings that can extend toward one another to engage tissue therebetween and thereby form a passageway through the tissue. In an exemplary embodiment, a distance between the proximal and distal wings is adjustable during rotation of the elongate tubular body.

While the proximal and distal portions can have a variety of configurations, in one embodiment, the proximal and distal portions each include at least one tab adapted to couple with at least one elongate tubular body extending therethrough to secure the proximal and distal portions in a fixed position relative to the at least one elongate tubular body. In another embodiment, the proximal portion can be adapted to be disposed in a first section of cut body lumen and the proximal wings can be adapted to engage the first section of body lumen. The distal portion can be adapted to be disposed in a second section of cut body lumen and the distal wings can be adapted to engage the second section of body lumen. The proximal and distal wings can each have a plurality of tissue engaging mechanisms configured to grasp tissue as the proximal and distal wings are formed.

The s-shaped slits can also have a variety of configurations. For example, the plurality of asymmetrical s-shaped slits formed in the proximal and distal portions can be adapted to bend at a location offset from a mid-point of each slit. In still another embodiment, the plurality of asymmetrical s-shaped slits can extend longitudinally along the elongate tubular body in a proximal-distal direction and can be spaced axially around the elongate tubular body.

A system for joining tissue is also provided and in one embodiment, the system can include an inner elongate tubular body defining a fluid flow lumen therethrough. The system can also include an outer elongate tubular body disposed around the inner elongate tubular body. The outer elongate tubular body can include proximal and distal portions adapted to expand upon rotation to fixedly engage the inner elongate tubular body and to form proximal and distal wings that extend toward one another to engage tissue therebetween. In one embodiment, the outer elongate tubular body can include a plurality of slits formed in each of the proximal and distal portions and configured to allow the proximal and distal portions to expand to form proximal and distal wings. The slits can extend, for example, longitudinally along the outer elongate tubular body in a proximal-distal direction, and they can be spaced axially around the elongate tubular body. In another embodiment, the inner elongate tubular body can include at least one slot formed therein. The outer elongate tubular body can include at least one tab formed thereon and adapted to engage the at least one slot to fixedly anchor the outer elongate tubular body to the inner elongate tubular body.

The system can also include an actuator removably coupled to the inner elongate tubular body and adapted to guide the inner elongate tubular body and the outer elongate tubular body into a body lumen. In one embodiment, the actuator includes an elongate shaft attached to the distal portion of the outer elongate tubular body. In another embodiment, the actuator includes an outer shaft removably coupled to the proximal portion of the outer elongate tubular body, and adapted to slide and rotate relative to the elongate shaft to expand the proximal and distal portions of the outer elongate tubular body.

A method for forming an anatomosis between two body lumens is also provided, and in one embodiment the method can include positioning an elongate tubular body within at least one body lumen (e.g., the esophagus, the prostate, or a blood lumen). The proximal and distal portions of the elongate tubular body can be rotated, e.g., using an actuator, to cause the proximal and distal portions to expand to form proximal and distal wings that extend toward one another to engage at least one body lumen therebetween and thereby form a fluid flow pathway through the at least one body lumen. In one embodiment, the proximal and distal wings can include tissue engaging mechanisms that grasp tissue as the wings are formed. The wings can be formed by, for example, compressing the proximal and distal portions as they are rotated to form proximal and distal wings. The method can also include adjusting a distance between the proximal and distal wings. In other embodiments, the method can include anchoring the at least one body lumen to the elongate tubular body prior to rotating the proximal and distal portions. In one embodiment, positioning the elongate body can include extending the elongate body between two openings in first and second body lumens to be joined.

In yet another embodiment, a method for occluding a body lumen is provided and includes advancing an elongate tubular body into a body lumen to be occluded, and rotating proximal and distal portions of the elongate tubular body to cause the proximal and distal portions to expand to form proximal and distal wings that extend toward one another to engage the body lumen therebetween. The elongate tubular body can have an inner lumen that is occluded such that fluid is prevented from flowing through the elongate tubular body, thereby occluding the body lumen.

BRIEF DESCRIPTION OF THE DRAWINGS

The invention will be more fully understood from the following detailed description taken in conjunction with the accompanying drawings, in which:

FIG. 1 is a side view of one exemplary embodiment of an anastomotic device in an initial, unformed configuration;

FIG. 2 is a cross-sectional view of the anastomotic device of FIG. 1 prior to deployment;

FIG. 3 is an end view of the anastomotic device of FIG. 1 following deployment;

FIG. 4 is a cross-sectional view of the anastomotic device of FIG. 1 showing an inner tubular body;

FIG. 5 is a side view of the anastomotic device of FIG. 1 following deployment;

FIG. 6 is a cross-sectional view of central bend points of the wings of the anastomotic device of FIG. 5 following deployment;

FIG. 7 is a cross-sectional view of central bend points of wings of another embodiment of an anastomotic device following deployment;

FIG. 8 is a cross-sectional view of the anastomotic device of FIG. 5;

FIG. 11 is a side view of the anastomotic device of FIG. 1 and a distal portion of the actuator of FIG. 10;

FIG. 12 is a cross-sectional view of the anastomotic device and the inner shaft of FIG. 11;

DETAILED DESCRIPTION

Figure 9:
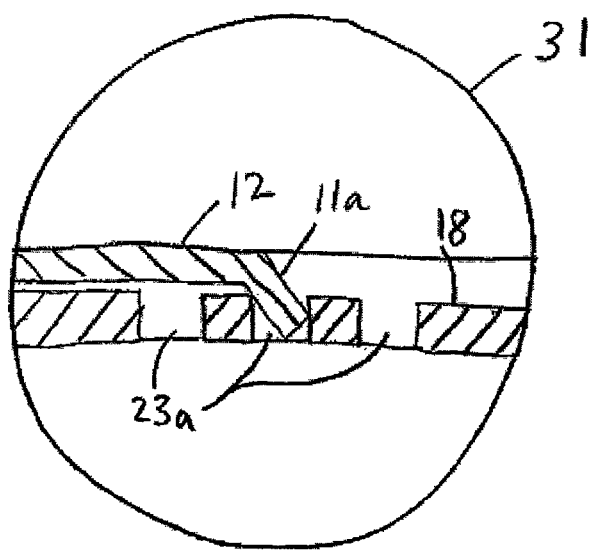
FIG. 9 is an enlarged view of a portion of the anastomotic device of FIG. 8.
Figure 10:
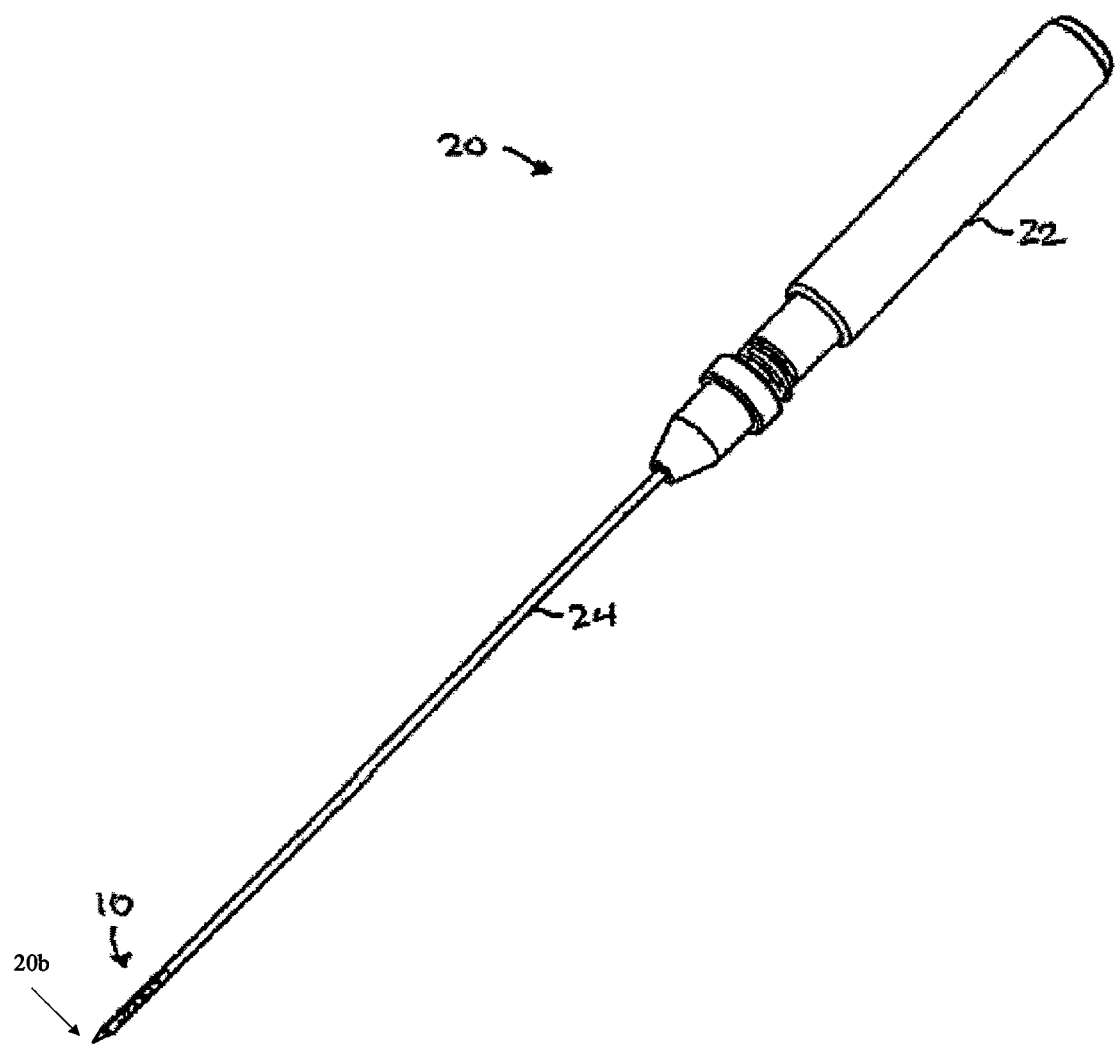
FIG. 10 is a perspective view of one exemplary embodiment of an actuator for deploying an anastomotic device, showing the anastomotic device of FIG. 1 coupled thereto.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope is defined solely by the claims. The features illustrated or described in connection with one exemplary embodiment may be combined with the features of other embodiments. Such modifications and variations are intended to be included within the scope of the present application.

The present invention provides methods and devices for joining body lumens in tissue (living or synthetic). In general, the anastomotic device can be in the form of an elongate body that can be adapted to be disposed through a body lumen (natural or artificial). The elongate body can include distal and proximal portions that are configured to radially expand to engage tissue therebetween and thereby join body lumens. FIG. 1 illustrates one exemplary embodiment of such an anastomotic device 10. The device 10 is illustrated in an initial, un-deployed configuration, and as shown the device 10 is in the form of a generally elongate tubular body 12 with an open proximal end 10a and an open distal end 10b. The tubular body 12 can be formed from a variety of materials including absorbable and non-absorbable materials. In an exemplary embodiment, the device 10 is formed from a deformable material that undergoes plastic deformation (i.e., deformation with negligible elastic component). Exemplary materials include, by way of non-limiting example, any resorbable (e.g., biocompatible and/or bioabsorbable) materials, including, for example, titanium (and titanium alloys), magnesium alloys, stainless steel, polymeric materials (synthetic and/or natural), shape memory material such as nitinol, ceramic, etc. Materials which are not normally radiopaque, e.g., magnesium alloy, may be enhanced and made x-ray visible with the addition of x-ray visible materials, such as particles of iron oxide, stainless steel, titanium, tantalum, platinum or any other suitable equivalents. The device 10 can also be manufactured using various techniques. For example, the device 10 can be formed from a piece of tubing, or it can be formed from sheet stock material. The developed surface of the final tubular shape may be stamped and folded into position. Various joining processes such as welding, soldering, etc. may be used to join any seams.

As indicated above, the device 10 can include one or more portions that expand to engage tissue therebetween and thereby anastomose body lumens. In the embodiment shown in FIG. 1, the device 10 includes proximal and distal portions 12a, 12b that are configured to expand to engage tissue therebetween. While various techniques can be used to allow the proximal and distal portions 12a, 12b to expand, in an exemplary embodiment the proximal and distal portions 12a, 12b each include a plurality of slits 14a, 14b formed therein and configured to allow portions of the elongate tubular body 12 between the plurality of slits 14a, 14b to radially expand, as will be discussed below. A mid-portion 13 of the tubular body 12, located between the proximal and distal portions 12a, 12b, can be configured to be positioned between two cut body lumens, e.g., within an anastomosis, so it can have a fixed or adjustable length that corresponds to a thickness of the tissue walls. The mid-portion 13 can have openings in the form of holes and/or slots to allow it to expand/retract (e.g., with compression and/or torsion) and have variable length and/or diameter, or the mid-portion 13 can be free from any cut-outs and be non-expanding/non-retracting with a fixed length and diameter.

The slits 14a, 14b in the proximal and distal portions 12a, 12b can extend in any direction, and each portion 12a, 12b can include any number of slits. Preferably, the slits 14a, 14b are configured such that certain portions of the elongate tubular body 12 between the slits 14a, 14b will extend outward away from a central axis A of the tubular body 12 when the body 12 is axially compressed, and preferably rotated as well. As a result, one or more wings will form in each of the distal and proximal portions 12a, 12b to engage tissue therebetween. The device 10 can also include tabs 15a, 15b in the distal and proximal portions 12a, 12b to aid in forming the wings, as discussed further below. In an exemplary embodiment, as shown in FIG. 1, the slits 14a, 14b are curved in S-shapes that extend transverse to a central axis A of the elongate tubular body 12 such that they at least partially extend around the elongate tubular body 12. The slits 14a, 14b can extend longitudinally along the elongate tubular body 12 in a proximal-distal direction, and they can be spaced axially around the elongate tubular body 12. More preferably, the slits 14a in the distal portion 12a extend in a first direction around a circumference of the elongate tubular body 12 and the slits 14b in the proximal portion 12b extend in a second, opposite direction around the circumference of the elongate tubular body 12. Such a configuration allows the tubular body 12 to be rotated in a first direction to cause only one of the proximal and distal portions 12a, 12b to radially expand, and then to be rotated in a second direction to cause the other one of the proximal and distal portions 12a, 12b to radially expand. Furthermore, the slits 14a, 14b in an exemplary embodiment are asymmetrical such that the upper or lower curve of a slit's S-shape is greater in length than its opposite side. This allows the slits 14a, 14b to bend at a location offset from a mid-point of each slit, thereby providing for generally uniform formation of the wings. A person skilled in the art will appreciate that the slits 14a, 14b can have a variety of other shapes and sizes, and that they can extend in various directions, such as helical or parallel to the central axis A of the tubular body. The number and configuration of the slits 14a, 14b can be chosen so that a certain number of wings can form at particular areas around the circumference of the device 10. The slits 14a, 14b can also include additional curved slits extending from each end of the main slits 14a, 14b to ensure that the end profile of the wings is aligned close to the elongate body 12 of the anastomotic device 10 following deployment. This can help ensure a fluid tight seal. The slits 14a, 14b can also have a thickness that narrows the width of the tubing section between slits thus encouraging the wings to bend outward at this point.

FIGS. 2 and 3 show distal end views of the device 10 in its pre-deployed configuration and following partial or full deployment, respectively. In the pre-deployed configuration shown in FIG. 2, the elongate tubular body 12 has a diameter that is configured to fit within a body lumen in tissue and that may also be configured to fit within an introducer sheath for guiding the device 10 to an anastomotic site, as will be discussed in more detail below. FIG. 3 illustrates the distal portion 12b radially expanded to form the distal wings. When the proximal portion 12a is radially expanded to form the proximal wings, the proximal wings can be aligned with the distal wings to facilitate lumen joining. In such a case, the distal end view of the device 10 would look as shown in FIG. 3 both before and after deployment of the proximal wings. The proximal wings can also be offset radially from the distal wings. In the illustrated embodiment, the slits 14a, 14b are configured such that the proximal and distal portions 12a, 12b each include three wings, however the proximal and distal portions can include any number of wings.

Referring again to FIG. 1, the proximal portion 12a, the distal portion 12b, and/or the mid-portion 13 of the anastomotic device 10 can optionally include tissue engaging mechanisms 17 formed or attached thereon which can be configured to grasp (e.g., grip, hold, penetrate, and/or puncture) tissue engaged by the device 10. The device 10 can include any number tissue engaging mechanisms 17, and the tissue engaging mechanisms 17 can have any configuration on the device 10. For example, as shown in FIG. 1, the tissue engaging mechanisms 17 can be in the form of protrusions, e.g., raised bumps and/or a textured surface, on some or all of an exterior surface of the elongate tubular body 12 that can grip tissue. In another example, the protrusions 17 can be in the form of gripping hooks attached to the elongate body 12 that can penetrate and/or puncture tissue. Preferably, the protrusions 17 are formed on the proximal and distal portions 12a, 12b of the elongate tubular body 12 such that the protrusions 17 are on the wings when deployed. The protrusions 17 can be configured on the elongate tubular body 12 to only engage tissue when rotated in one direction. The protrusions 17 can facilitate anchoring of the anastomotic device 10 at an anastomotic site, and they can also be used to facilitate sealing of an anastomotic site. During deployment of the device 10, the protrusions 17 can grip tissue around the anastomotic device 10, and upon rotation of the wings can twist tissue in a spiral motion, thereby causing tissue to compress around the outer elongate tube 12 and seal the site. One or more sutures (e.g., purse string sutures) can help secure the elongate tubular body 12 to tissue such that when a suture is pulled tight around the tissue, tissue can be compressed into a protrusion 17 (e.g., a slot) or be prevented from moving by a protrusion 17 (e.g., a dimple). The protrusions 17 can also be configured so as to only engage tissue when rotated in one direction.

As illustrated in FIG. 4, the elongate body 12 can also include one or more tabs 11a, 11b in the distal and proximal portions 12a, 12b to aid in forming the wings. Any number of the tabs 11a, 11b can be formed on an inner surface of the elongate tubular body 12 around any portion of its circumference. The number of tabs 11a, 11b can be the same or can vary between the proximal and distal portions 12a, 12b. The tabs 11a, 11b can generally point in a downward direction (i.e., away from one another), and they can couple with an inner, generally elongate tubular body 18 extending through the elongate tubular body 12 (also referred to as the outer elongate body 12) to secure the proximal and distal portions 12a, 12b in a fixed position relative to the inner elongate tubular body 18. The inner elongate body 18 can include at least one slot 23a, 23b formed in its proximal and distal portions 25a, 25b to mate with the tabs 11a, 11b, as discussed further below.

The inner elongate body 18 and the outer elongate body 12 are both shown in cross-sectional, undeployed configurations in FIG. 4. The inner elongate body 18 can be disposed in the outer elongate body 12 and can optionally be attached to the inner elongate body 18, e.g. at the mid-portion 13 of the outer elongate body 12 and at a mid-portion 27 of the inner elongate body 18 using a temporary or permanent connecting element such as a biocompatible adhesive 19. Similar to the outer elongate body 12, the inner elongate body 18 between the open distal end 21b and the open proximal end 21a. The inner elongate body 18 between the open distal end 21b and the open proximal end 21a defines a fluid lumen therethrough extending along the central axis A.

The tabs 11a, 11b in the proximal and distal portions 12a, 12b of the outer elongate body 12 are adapted to engage the slots 23a, 23b in the proximal and distal portions 25a, 25b of the inner elongate body 18. The slots 23a, 23b can be cut through a wall of the inner elongate body 18 and can have any size, shape, and configuration. In this embodiment, the slots 23a, 23b are substantially rectangular and are arranged in substantially straight lines around the circumference of the inner elongate body 18. When one or more of the tabs 11a, 11b are engaged with one or more of the slots 23a, 23b, the outer elongate body 12 is fixedly anchored to the inner elongate body 18. As such, the position of the wings can be adjusted and fixedly held as explained further below. One tab typically engages one slot, although each of the slots 23a, 23b can be configured to engage more than one of the tabs 11a, 11b, e.g., by adjusting the width of the tabs 11a, 11b and/or the slots 23a, 23b so that multiple tabs 11a, 11b can fit in one of the slots 23a, 23b.

FIG. 5 shows the anastomotic device 10 in a deployed configuration. The inner elongate body 18 may or may not be disposed within the device 10 and, if present, may or may not be visible at one or both of the proximal and distal ends 10a, 10b (it is present but not visible in FIG. 5). In the deployed configuration, the proximal portion 12a is expanded to form proximal wings 16a, and the distal portion 12b is expanded to form distal wings 16b. The wings 16a, 16b are formed by the material between the slits 14a, 14b, which is deformed outward as the outer elongate body 12 is compressed and preferably rotated. The wings 16a, 16b can be concurrently or sequentially formed, e.g., deploying the distal wings 16b before the proximal wings 16a.

The size and shape of the wings 16a, 16b can vary depending on the location and length of the slits 14a, 14b. In an exemplary embodiment, the size and shape of the wings 16a, 16b can be maximized to maximize the contact area between the wings 16a, 16b and the tissue surrounding the anastomotic site within which the device 10 is deployed. In this embodiment, the wings 16a, 16b are substantially ovular-shaped and have a generally planar relationship with each other such that the wings 16a, 16b extend substantially parallel to one another, i.e., they are formed in parallel planes. In another configuration, the wings 16a, 16b can converge or diverge with respect to one another. The proximal wings 16a can be circumferentially offset, e.g., offset rotationally, relative to the distal wings 16b to further maximize the contact area around the anastomotic ring. The proximal and distal wings 16a, 16b are also preferably configured to be positioned a distance apart from one another. The length of the mid-portion 13 determines of the distance between a base portion of the wings 16a, 16b while compression/rotation of the device 10 determines the distance between a tip portion of the wings 16a, 16b. Furthermore, a cut profile on one side of a perpendicular axis B of the elongate tubular body 12 can generally be a mirror image of the opposite side. When the wings 16a, 16b are deployed, the central bend points may be positioned directly opposite the bend points for the other side as illustrated in FIG. 6. Alternatively, the slits 14a, 14b on each side may be offset so that once deployed the central bend points are also offset from each other as shown in FIG. 7. As the ends of the elongate tubular body 12 are rotated, these central sections generally close toward each other.

FIG. 8 shows a cross-sectional view of the deployed device 10 of FIG. 5. The asymmetric profile of the slits 14a, 14b can allow the wings 16a, 16b to form such that interior base bend angles $\alpha 1$, $\alpha 2$ are less than respective exterior base bend angles β1, β2. As a result, the wings 16a, 16b will also extend toward one another. The interior base bend angles α1, α2 can be the same or different in the proximal and distal portions 12a, 12b, as can the exterior base bend angles β1, β2. If the exterior base bend angles β1, β2 are each about 90 degrees, the wings 16a, 16b extend substantially parallel to each other, while acute and obtuse exterior base bend angles β1, β2 can allow the wings 16a, 16b to be angled toward each other at one end and away from each other at the opposite end. In FIG. 8, the inner elongate body 18 is disposed in the outer elongate body 12, and the proximal and distal tabs 11a, 11b are engaged with proximal and distal slots 23a, 23b. A cutaway section 31 of the proximal portion 12a in FIG. 9 shows one of the proximal tabs 11a engaged with one of the proximal slots 23a, thereby fixedly anchoring the outer elongate body 12 to the inner elongate tubular body 18.

A distance between the wings 16a, 16b can be controlled in a variety of ways during rotation of the outer elongate body 12. The distance between the wings 16a, 16b can be constant, or the distance can vary. For example, the distance can be controlled by rotating and compressing the outer elongate body 12 to varying degrees, thereby varying the distance between the wings 16a, 16b. In another embodiment, the distance can be controlled by expanding or contracting the mid-portion 13. The distance could also be controlled by forming the wings 16a, 16b and anchoring the tabs 11a, 11b in different rows of slots 23a, 23b, thereby holding the wings 16a, 16b in a substantially fixed position. FIG. 4 shows multiple rows of the slots 23a for receiving the tabs 11a at different longitudinal positions. Referring to FIG. 8, a distance D1 between the proximal and distal wings 16a, 16b can be substantially the same as a distance D2 between the proximal and distal wings 16a, 16b at another location along the circumference of the outer elongate body 12. Alternatively, the distance D1 can be greater than D2 or less than D2 by disengaging the tabs 11a, 11b at either or both the proximal and distal portions 12a, 12b and reengaging one or more of the tabs 11a, 11b with another one or more of the slots 23a as appropriate to increase or decrease the distance.

As indicated above, the wings 16a, 16b on the anastomotic device 10 can be formed by compressing and preferably rotating the device 10. While various techniques can be used to deploy and actuate the device 10, in one exemplary embodiment the anastomotic device 10 is removably coupled to an actuator that can be adapted to guide the device 10 into a body lumen and to apply an axial and rotational force to the elongate tubular body 12 to cause the elongate tubular body 12 to extend outwardly. FIGS. 10-12 and 15-21 illustrate one exemplary embodiment of an actuator 20 for deploying the anastomotic device 10. In general, the actuator 20 includes a proximal portion in the form of a handle 22, and an elongate shaft extending distally from the handle 22. A distal end of the actuator 20 includes a digital gripper assembly 28 that is adapted to removably couple to the anastomotic device 10. The elongate shaft includes an outer shaft or former 24 that is disposed around and coupled to an assembly shaft 25, which itself is disposed around an inner shaft 26. The inner shaft 26 is effective to hold a portion of the device 10 in a fixed position by expanding the assembly shaft 25 (and possibly also the former 24) to allow the digital gripper assembly 28, which is formed on the distal end of the assembly shaft 25, to engage the device 10, as described further below. With both the inner and assembly shafts 26, 25 disposed within the former 24, the former 24 can be effective to apply axial and/or rotational forces to the anastomotic device 10 to deploy the anastomotic device 10.

The former 24 can have a variety of configurations, but it is preferably adapted to detachedly couple to the proximal end 10a of the anastomotic device 10. While various techniques can be used to couple the former 24 to the anastomotic device 10, FIGS. 11 and 12 illustrate one exemplary technique. As shown, the former 24 includes one or more protrusions 24a that can extend into one or more notches formed between tabs 15a formed in the proximal end 10a of the device 10 such that the protrusions 24a and tabs 15a interlock. Similarly, the digital gripper assembly 28 can also have a variety of configurations, but it is shown as an expandable tubular member having one or more protrusions 28b that can extend proximally into one or more notches formed between tabs 15b formed in the distal end 10b of the device 10 such that the protrusions 28b and tabs 15b interlock. The distal gripper assembly 28 can be attached to or formed on the distal end of the assembly shaft 25, which is slidably disposed through the former 24. For example, the distal gripper assembly 28 can be attached to the anastomotic device 10 using a threaded attachment. Furthermore, the distal gripper assembly 28 can include one or more thinned or weakened regions to help it collapse for its detachment and removal from the outer elongate body 12 as described further below. The thinned or weakened region(s) can be achieved by reducing the amount of material at that region, or by scoring or otherwise removing some of the material used to form the distal gripper assembly 28.

Figure 13:
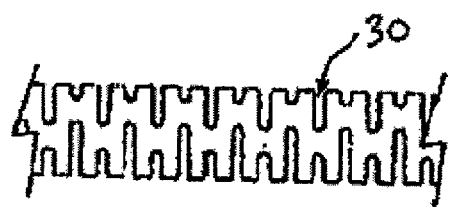
FIG. 13 is a side view of one embodiment of a former tube for use with the actuator of FIG. 10.
Figure 14:
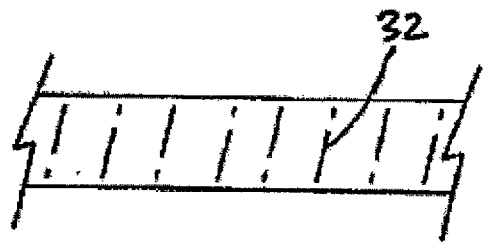
FIG. 14 is a side view of another embodiment of a former tube for use with the actuator of FIG. 10.
Figure 15:
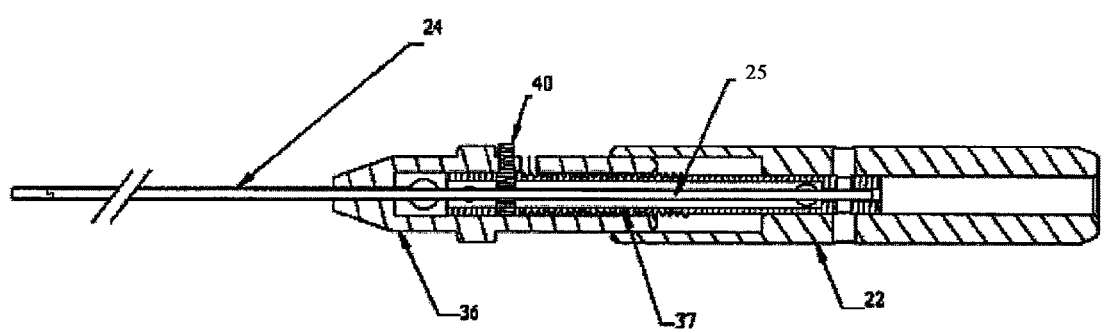
FIG. 15 is a cross-sectional view of the handle portion of the actuator of FIG. 10.

The former 24 and/or the assembly shaft 25 can also be configured to provide maximum flexibility during clinical use, while the inner shaft 26 can be rigidly configured to provide structural support to the former 24 and/or the assembly shaft 25. For example, the former 24 and/or the assembly shaft 25 can be formed from a flexible material, or the former 24 and/or the assembly shaft 25 can include one or more flexible regions formed thereon. FIGS. 13 and 14 show exemplary embodiments of flexible regions. In the embodiment shown in FIG. 13, the tube includes an interrupted slotted pattern 30. In the embodiment shown in FIG. 14, the tube includes a spiral slit or interrupted spiral slit 32 cut through the wall of the tube. Such configurations provide flexibility along all or portions of the former 24 and/or the assembly shaft 25, but can also ensure that an axial and/or rotational force applied to one end of the former 24 will be transmitted along the length of the former 24 and/or the assembly shaft 25 to the other end.

In order to rotate the former 24 relative to the assembly shaft 25 and the inner shaft 26 and thereby form the wings 16a, 16b, the handle 22 of the actuator 20 can optionally include an actuation mechanism formed thereon. In an exemplary embodiment shown in FIGS. 15-18, the handle 22 includes an outer collar 36 rotatably disposed therearound and having guide tracks 38 formed therein. The outer collar 36 can be coupled to a proximal portion of the former 24 such that rotation of the collar 36 is effective to rotate the former 24. The proximal end of the assembly shaft 25 can also include an inner collar 37 that is attached to the assembly shaft 25 and that includes a pin 40 formed thereon or extending therefrom. The pin 40 extends through and is positioned within the guide tracks 38. Since the position of the pin 40 is fixed due to the assembly shaft 25 being fixed, movement of the outer collar 36, and thus the former 24, is governed by the configuration of the guide tracks 38 which can move relative to the fixed pin 40. As a result, the guide tracks 38 can be used to control the axial and rotational forces applied to the anastomotic device 10 coupled to the distal end of the former 24.

Figures 16, 17, 18:
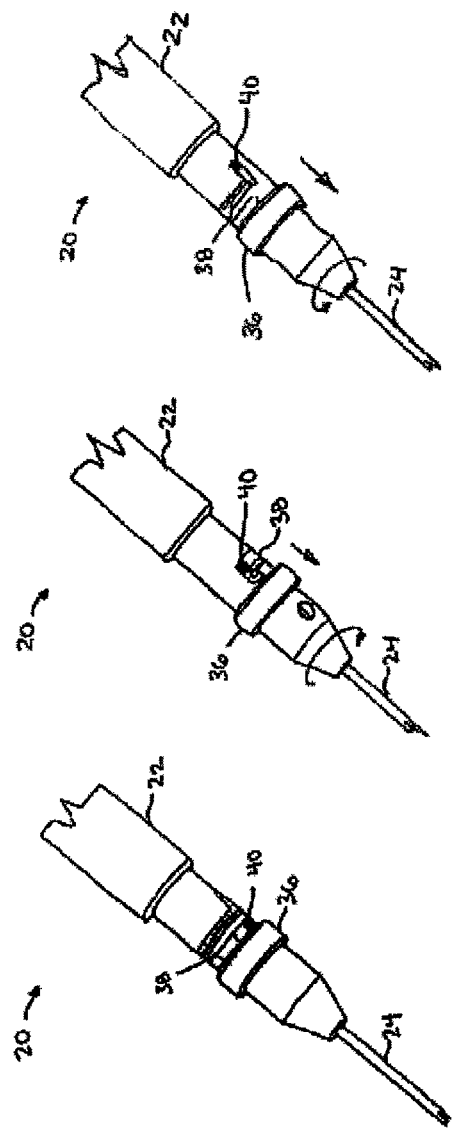
FIG. 16 is a perspective view of a proximal portion of the actuator of FIG. 15 in an initial, starting position.
FIG. 17 is a perspective view of the proximal portion of the actuator shown in FIG. 16 following deployment of the distal wings of an anastomotic device.
FIG. 18 is a perspective view of the proximal portion of the actuator shown in FIG. 17 following deployment of the proximal wings of an anastomotic device.

As shown in FIGS. 16-18, the guide tracks 38 can have a configuration that allows the collar 36 to rotate in a first direction, e.g., counter clockwise, to deploy the distal wings 16b of the anastomotic device. The distal wings 16a, 16b can be deployed before or after the proximal wings 16a although they are deployed first in this example. In particular, as the outer collar 36 is rotated counter clockwise, the former tube 24 will rotate in a counter-clockwise direction, thereby rotating the proximal end 10a of the anastomotic device 10 to expand the distal wings 16b of the anastomotic device 10. The gripper 28 will remain in a fixed position, thus holding the distal end 10b of the device 10 in a fixed position while the proximal end 10a is rotated. As previously discussed, since the slits 14a, 14b in the distal and proximal portions 12a, 12b preferably extend in opposite directions, rotation of the anastomotic device 10 in a first direction will only deploy the distal wings 16b. Once the outer collar 36 is fully rotated, the guide tracks 38 can allow distal movement of the outer collar 36, while the guide pin 40 remains in a fixed position at all times, thus allowing the outer collar 36 to be advanced distally. As a result, the former tube 24 will apply compressive forces on the anastomosis device 10, thereby causing the distal wings 16b to collapse into a substantially planar configuration.

The guide tracks 38 can then allow the outer collar 36 to rotate in an opposite direction, e.g., a clockwise direction, to cause the former tube 24 to rotate clockwise. As the former 24 rotates clockwise, the proximal wings 16a will expand. Once the outer collar 36 is fully rotated, the guide tracks 38 can allow distal movement of the outer collar 36 therein, thus allowing the outer collar 36 to be advanced distally. As a result, the former tube 24 will apply compressive forces on the anastomotic device 10, thereby causing the proximal wings 16a to collapse into a substantially planar configuration in which they extend transverse to the axis A (see FIGS. 1 and 4) of the device 10.

A person skilled in the art will appreciate that the guide tracks 38 can have a variety of other configurations. For example, rather than allowing rotation, and then distal movement, the guide tracks 38 can extend at an angle around the handle 22 to allow rotational and compressive forces to be simultaneously applied to the anastomotic device 10. A person skilled in the art will appreciate that a variety of other techniques can be used to actuate the former 24 to deploy the device.

Once the device 10 is deployed, the actuator 20 can be removed. For example, the distal gripper assembly 28 can be configured such that it can disengage from the outer elongate body 12 when a force is applied thereto. In use, the distal gripper assembly 28 can be collapsed by removing the inner shaft 26, which allows the distal gripper assembly 28 to return to an unexpanded state in which it can be retracted through the device 10. During use, the distal gripper assembly 28 can be rotated relative to the anastomotic device 10 so as to unscrew the distal gripper assembly 28 from the anastomotic device 10. Once detached, the distal gripper assembly 28 (and the former 24) can be removed from the patient, leaving the anastomotic device 10 in position at the anastomotic site. A person skilled in the art will appreciate that a variety of mating techniques can be used, including, for example, an interference fit, a mechanical interlock, etc.

Figure 19:
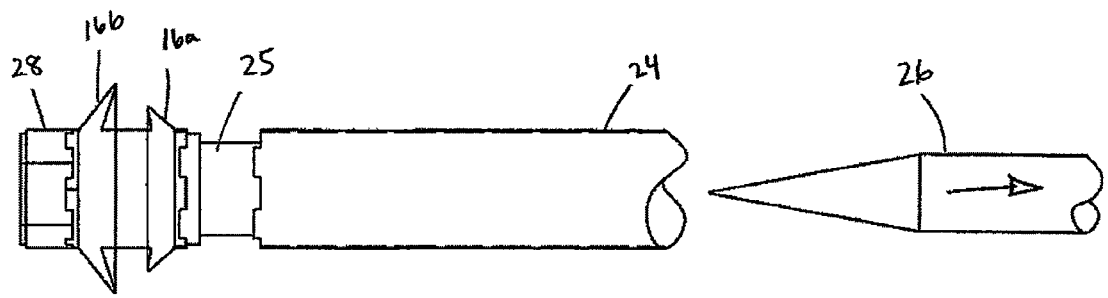
FIG. 19 is a side view of the anastomotic device of FIG. 1 and an inner shaft of the actuator of FIG. 10 being removed from the anastomotic device.
Figure 20:
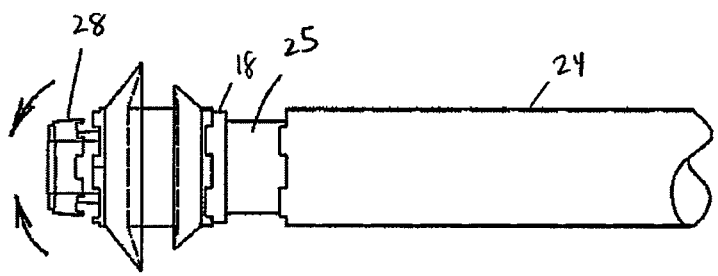
FIG. 20 is a side view of the anastomotic device of FIG. 19 and a distal gripper assembly of the actuator being removed from the anastomotic device.
Figure 21:
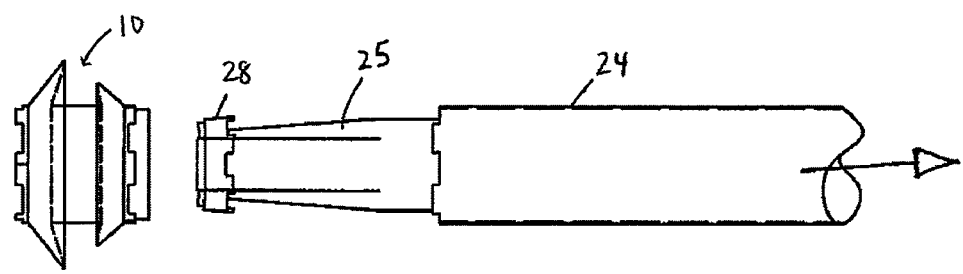
FIG. 21 is a side view of the anastomotic device of FIG. 20 and the remainder of the actuator being removed from the anastomotic device.

FIGS. 19-21 illustrate a distal portion of the outer shaft 24, the assembly shaft 25, and the inner shaft 26 of the actuator 20 in use with the anastomotic device 10. Following deployment of the anastomotic device 10, the actuator 20 is preferably disconnected and removed from the patient. In FIG. 19, the protrusions 24a on the former 24 are removed from the corresponding cut-outs formed between the tabs 15a in the proximal end 10a of the device 10. The inner shaft 26 can then be withdrawn from the assembly shaft 25 and the outer shaft 24 in a distal direction. Removing the inner shaft 26 can cause the distal end of the assembly shaft 25 to collapse inwards as shown by the directional arrows in FIG. 20. The diameter of the assembly shaft 25 can thereby be reduced so that it and the attached or coupled distal gripper assembly 28 can be moved through the inner elongate body 18. The entire remaining actuator assembly (e.g., the assembly and outer shafts 25, 24) can be withdrawn in a distal direction as shown in FIG. 21, thereby leaving the device 10 deployed and engaging tissue. The device 10 can also be removed from the body after deployment, if necessary. For example, the tabs 11a, 11b (if in use) can be disengaged from the slots 23a, 23b, the wings 16a, 16b can be collapsed to their original, flat, undeployed configuration, the protrusions 17 (and any sutures) can be disengaged from tissue if necessary, and the device 10 can be removed from the body.

The present invention also provides exemplary methods for joining body lumens in tissue. While various devices can be used to effect the method in one embodiment, the device 10 can be delivered to a lumen over a guidewire. The proximal end of the guidewire, which extends from the patient, can be inserted into an opening at the distal end 10b of the anastomotic device 10 or through the inner shaft 26 if it is hollow. The guidewire can extend through the shaft and handle 22 of the actuator 20, or in other embodiments it can exit through a side hole located either in the anastomotic device 10 or at the distal end of the former 24.

Figure 22:
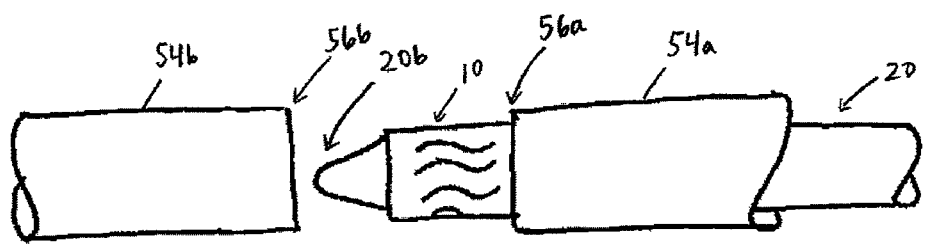
FIG. 22 is a side view of the anastomotic device of FIG. 1 and a portion of the actuator of FIG. 10, showing the anastomotic device positioned relative to two body lumens to be joined.

FIG. 22 illustrates the distal end of the actuator 20, coupled with the device 10, disposed in a proximal cut lumen 54a to be joined with a distal cut lumen 54b. Typically, the proximal and distal cut lumens 54a, 54b were previously part of a single, continuous lumen, but a diseased or otherwise unwanted portion of the lumen was cut away, leaving the two cut lumens 54a, 54b to be rejoined into a single lumen. The actuator 20 and the device 10, still disposed through in the proximal cut lumen 54a, can be advanced through the distal cut lumen 54b such that the device 10 is disposed at least partially in each of the cut lumens 54a, 54b. Preferably, the proximal portion 12a of the outer elongate tube 12 is substantially positioned in the proximal cut lumen 54a and the distal portion 12b of the outer elongate tube 12 is substantially positioned in the proximal cut lumen 54b. Ends 56a, 56b of the cut lumens 54a, 54b can be positioned to abut each other such that the mid-portion 13 of the outer elongate body 12 is substantially between the cut lumens 54a, 54b, either before either of the wings 16a, 16b are deployed or, preferably, after the distal wing 16b is deployed but before the proximal wing 16a is deployed. A suture can optionally be used to secure one or both cut lumens 54a, 54b to the outer elongate body 12. With the device 10 disposed in both of the cut lumens 54a, 54b, the wings 16a, 16b can be deployed and the cut lumens 54a, 54b can be joined. In this example the ends 56a, 56b are open, but if the ends 56a, 56b are closed (e.g., by staples, suture, etc.), a pointed tip 20b at a distal end of the inner shaft 26, or other cutting element, can be used to puncture the ends 56a, 56b when inserting the actuator 20 and the device 10 into the lumens 54a, 56b.

Figure 23:
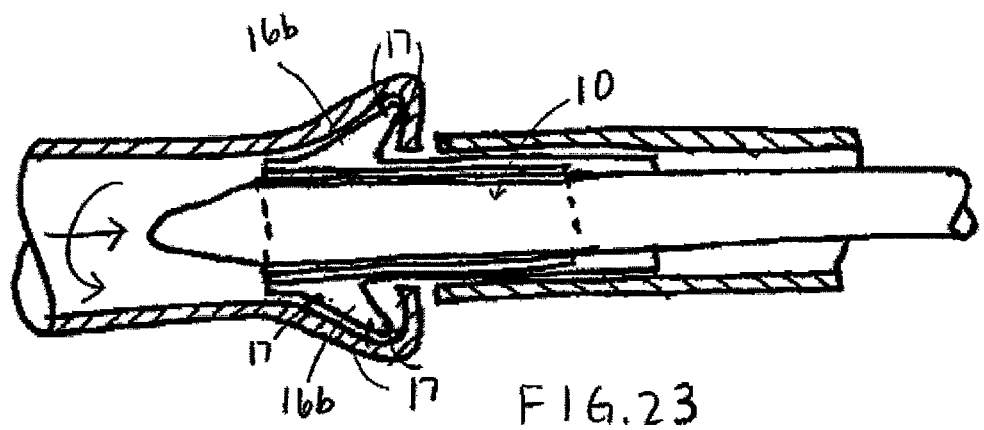
FIG. 23 is a cross-sectional view of the anastomotic device and the actuator of FIG. 22 following deployment of the distal wings.
Figure 24:
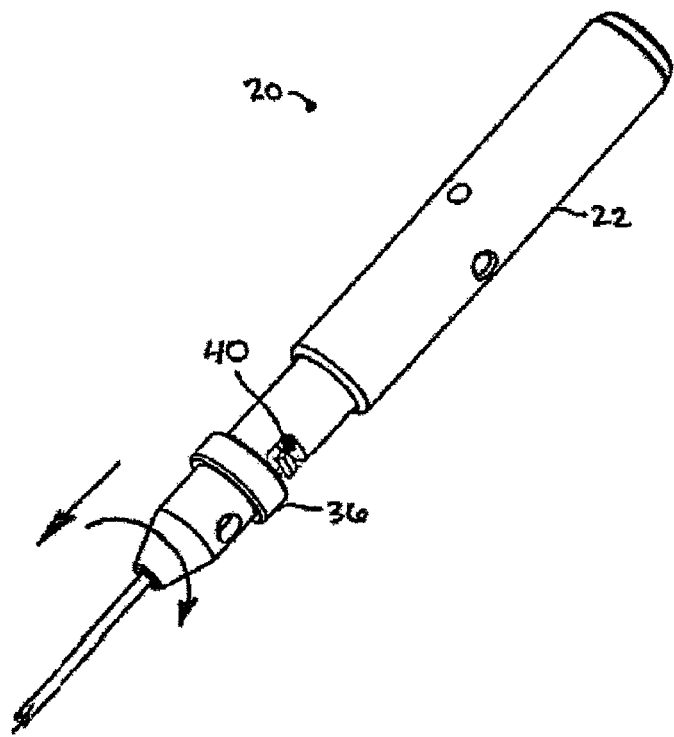
FIG. 24 is a perspective view of an actuator following deployment of the distal wings.

FIG. 23 illustrates the actuator 20 disposed in the cut lumens 54a, 54b with the distal wing 16b deployed. Once the anastomotic device 10 is positioned to be deployed, the outer collar 36 on the handle 22 of the actuator 20 can be rotated in a first direction, e.g., counter-clockwise as shown in FIG. 24, to cause the distal portion of the anastomotic device 10 to expand away from the central axis. A compressive force can simultaneously or subsequently be applied to the anastomotic device 10 to cause the expanded portions of the anastomotic device 10 to collapse, and thereby form distal wings 16b, as shown in FIG. 23. Suture and/or the protrusions 17 of the distal end 10b of the device 10 can be used to help grip the distal cut lumen 54b to help guide it into a winged configuration that substantially mirrors the configuration of the distal wing 16b.

Figure 25:
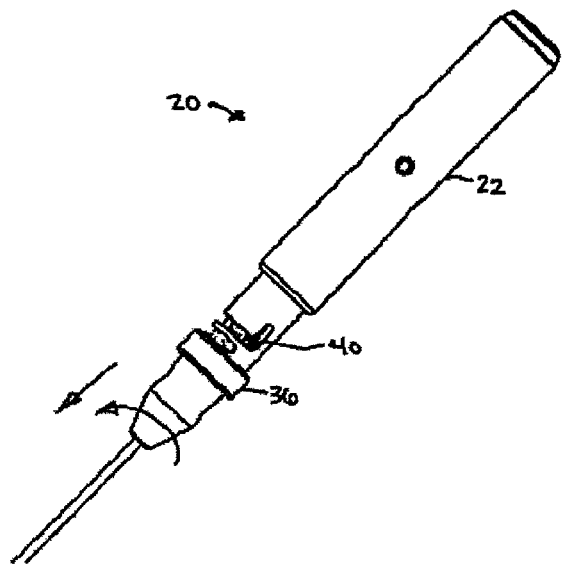
FIG. 25 is a perspective view of the actuator of FIG. 24 following full deployment of the proximal wings.
Figure 26:
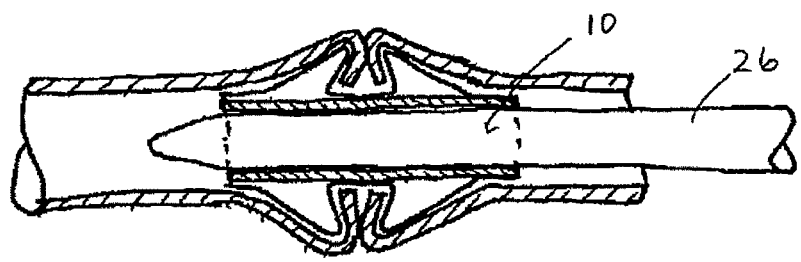
FIG. 26 is a cross-sectional view of the anastomotic device and the actuator of FIG. 23 following deployment of the proximal wings.
Figure 27:
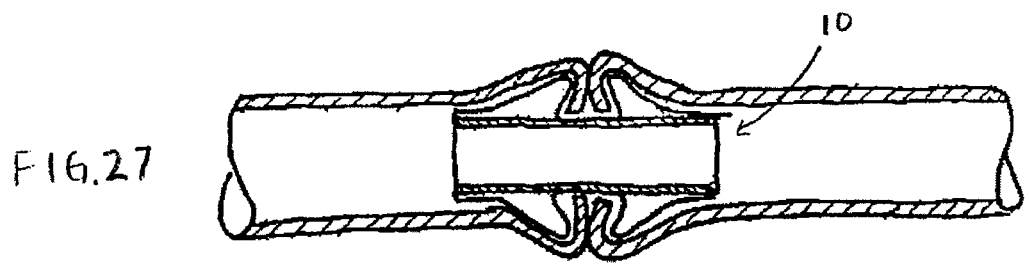
FIG. 27 is a cross-sectional view of the anastomotic device of FIG. 26 following detachment of the actuator.

Following deployment of one of the distal and proximal wings 16a, 16b, the other one of the wings 16a, 16b can be similarly deployed to anastomosis the lumens 54a, 54b. The proximal wings 16a can be deployed by rotating the actuator outer collar 36 in an opposite direction, e.g., a clockwise direction, as shown in FIG. 25. This in turn can cause the former 24 to rotate the proximal end of the anastomotic device 10 in a clockwise direction causing the proximal portion 12a of the anastomotic device 10 to expand outward. The former 24 can be simultaneously or subsequently advanced distally causing the expanded portions of the anastomotic device 10 to collapse and form the proximal wings 16a, as shown in FIG. 26. Thus, the distal and proximal wings 16a, 16b can extend toward one another and engage the tissue of the cut lumens 54a, 54b therebetween and thereby form a fluid flow pathway between the lumens 54a, 54b. As illustrated in FIG. 27, with the device 10 deployed and the anastomosis site sealed, the actuator 20 can be removed from the device 10 as previously discussed.

Figure 28:
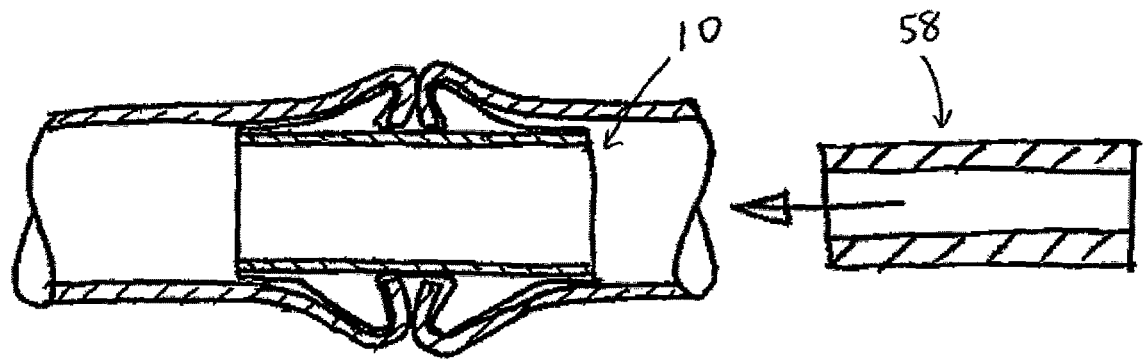
FIG. 28 is a cross-sectional view of the anastomotic device of FIG. 27 and a supplemental elongate tubular body prior to its insertion into the anastomotic device.
Figure 29:
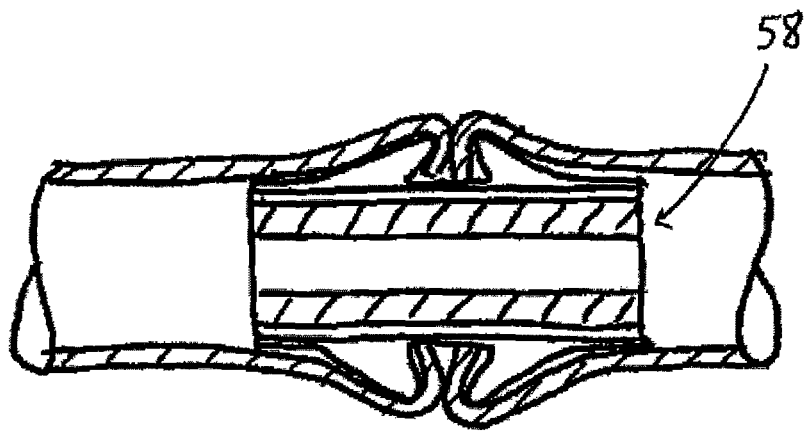
FIG. 29 is a cross-sectional view of the anastomotic device of FIG. 27 with the supplemental elongate tubular body of FIG. 28 disposed in the anastomotic device.

In some instances the lumen diameter at the anastomotic junction may desirably be reduced. One way this can be achieved is shown in FIG. 28 by inserting into the device 10 a supplemental elongate tubular body 58 having an open diameter smaller than the open diameter of the inner elongate body 18. The supplemental elongate body 58 can be formed from a variety of materials, including absorbable and non-absorbable materials, such as those described above. The supplemental elongate body 58 can be inserted through the proximal end 10a of the device 10 as shown, or it can be inserted through the distal end 10b. The supplemental elongate body 58 can be locked into position using any technique, such as with a latch or bayonet type of fixing to the device 10 (e.g., at an inside wall of the inner elongate body 18) or by increasing its diameter. Once in position as shown in FIG. 29, the lumen diameter is reduced from its pre-joining configuration at the point of the anastomotic junction. The supplemental elongate body 58 can be removed in a variety of ways, similar to how the device 10 can be removed, such as by inserting a rod, attaching its distal end to the supplemental elongate body 58, detaching the supplemental elongate body 58 from the inner elongate body 18, and removing the supplemental elongate body 58 from the body.

In yet another embodiment, the device can be used for total occlusion of a body lumen, such as the fallopian tube. For example, the device of FIGS. 28 and 29 can include a solid member adapted to be disposed therein to prevent fluid from passing therethrough. In particular, the supplemental elongate body 58 can be a substantially solid tubular member that is disposed within the device 10. Alternatively, the device 10 can have a solid inner member that prevents passage of fluid therethrough. In use, the device can be advanced into a lumen to be occluded, such as the fallopian tube. One set of wings can be deployed, and protrusions, if present, can engage the wall of the lumen. The second set of wings can also be deployed thereby compressing and capturing the wall of the lumen between both sets of deployed wings, and also anchoring the occluder device in position. As indicated above, the central portion of the device can be solid to prevent passage of fluid from one side to the other side.

Figure 30:
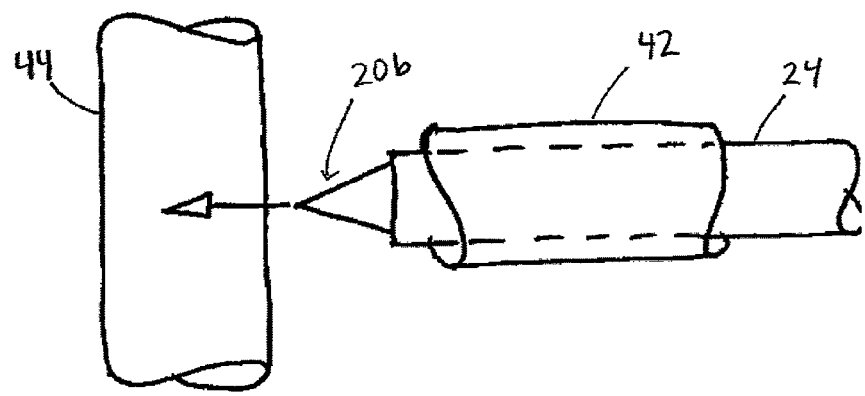
FIG. 30 is a side view of the anastomotic device of FIG. 1 and a portion of the actuator of FIG. 10, showing another embodiment of the anastomotic device positioned close to two body lumens to be joined.
Figure 31:
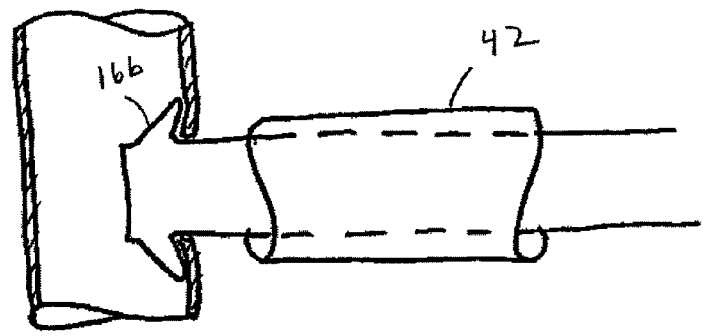
FIG. 31 is a partially cross-sectional view of the anastomotic device of FIG. 30 advanced into a body lumen and with the distal wings deployed.
Figure 32:
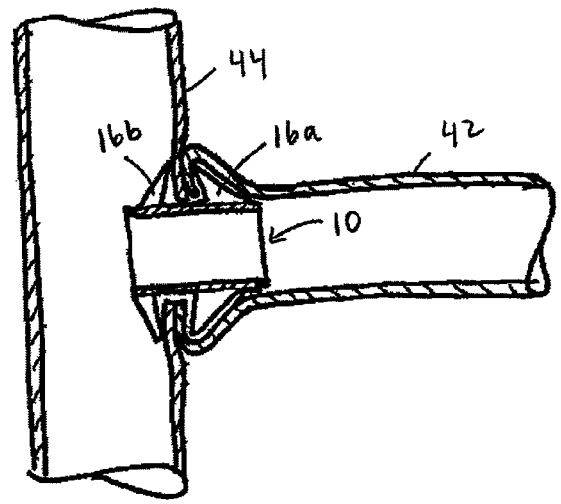
FIG. 32 is a cross-sectional view of the anastomotic device of FIG. 31 with the proximal wings deployed to engage the two body lumens.

In some embodiments, the device 10 can be used to create an end-to-side anastomotic junction as shown in FIGS. 30-32. The device 10 disposed around the actuator 20 can be advanced through a first section of body lumen 42 as described above. The pointed tip 20b of the inner shaft 26, or other cutting element, can optionally be used to puncture a wall of a second section of body lumen 44. Then as shown in FIG. 31, the device 10 can be advanced into the second section of body lumen 44 and the distal wings 16b can be deployed as described above. The first section of body lumen 42 can then be advanced to abut the second lumen 44 against its sidewall. The proximal wings 16a can then be deployed, thereby creating a compressed seal between the end section of the first lumen 42 and the wall of the second lumen 44 as shown in FIG. 32. Suture can be used to secure the sections of body lumen 42, 44 in position, e.g., at the mid-portion 13 of the outer elongate body 12.

The device 10 can also be used to create a side-to-side anastomotic junction similar to the end-to-side anastomotic junction described above. To form a side-to-side junction, the device 10 can be advanced through a first section of body lumen and the pointed tip 20b of the inner shaft 26, or other cutting element, can be used to puncture through its side wall and then through a side wall of a second section of body lumen. Distal wings can then be deployed within the first section of body lumen and proximal wings deployed within the second section of body lumen to create the side-to-side junction.

Figure 33:
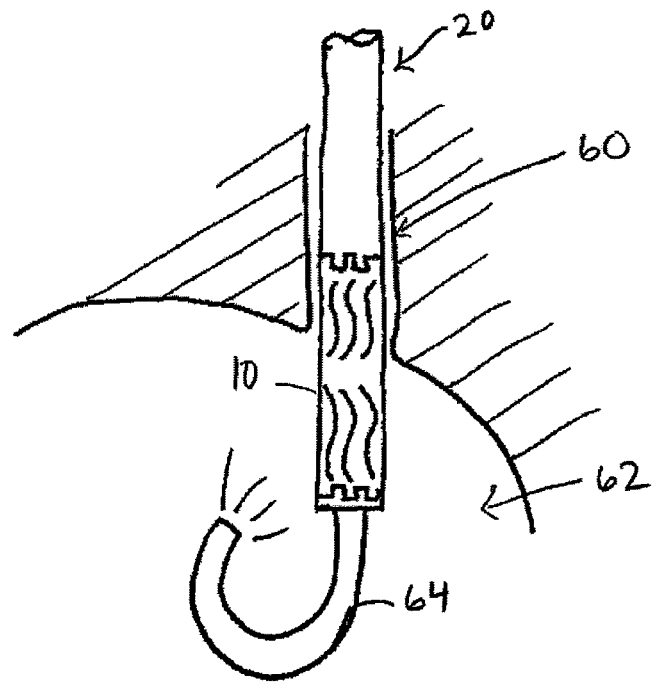
FIG. 33 is a partially cross-sectional view of the anastomotic device and the actuator portion of FIG. 11 disposed through an esophagus and within a stomach.
Figure 34:
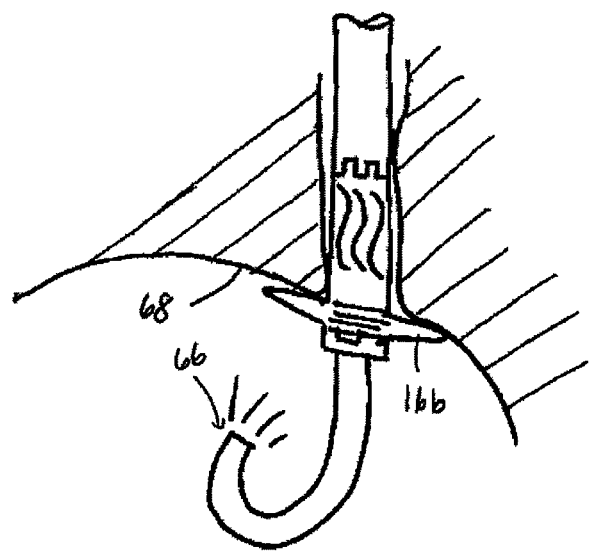
FIG. 34 is a partially cross-sectional view of the anastomotic device and the actuator portion of FIG. 33 with the distal wings deployed.
Figure 35:
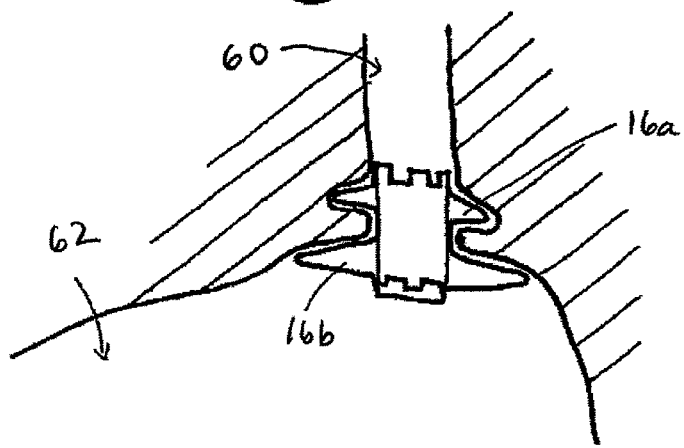
FIG. 35 is a partially cross-sectional view of the anastomotic device of FIG. 34 with the proximal wings deployed.

The anastomotic device 10 can also be used to restrict the size of an opening between two body tissues such as an esophagus 60 and a stomach 62 as shown in FIGS. 33-35. A flexible endoscope 64 can be advanced through the esophagus 60 and into the stomach 62. The actuator 20 in this embodiment is ideally hollow to accommodate the endoscope 64, which is typically advanced into the patient before the actuator 20 and the anastomotic device 10. The device 10, coupled to the actuator 20, can be advanced over the endoscope 64, down through the esophageal junction and into the stomach 62. The distal end of the scope 64 can be positioned so that its lens 66 can look back at the anastomotic ring assembly as illustrated in FIG. 34. In this way, medical personnel can have an internal view of the stomach 62 and/or the esophagus 60 to more accurately position the device 10 inside the body and deploy the distal wings 16b in the appropriate position. Once the distal wings 16b are deployed, the device 10 can be pulled back toward the esophagus 60 along the scope 64 until the deployed distal wings 16b make contact with a wall 68 of the stomach 62. The proximal wings 16a can then be deployed, thereby pushing tissue toward the mid-portion 13 of the anastomotic device 10 while compressing tissue between both sets of deployed wings 16a, 16b. Thus, a junction of fixed diameter can be formed between the esophagus 60 and the stomach 62 as shown in FIG. 35. With the tissue joined, the actuator 20 can be removed from the esophagus 60 as described above.

Figure 36:
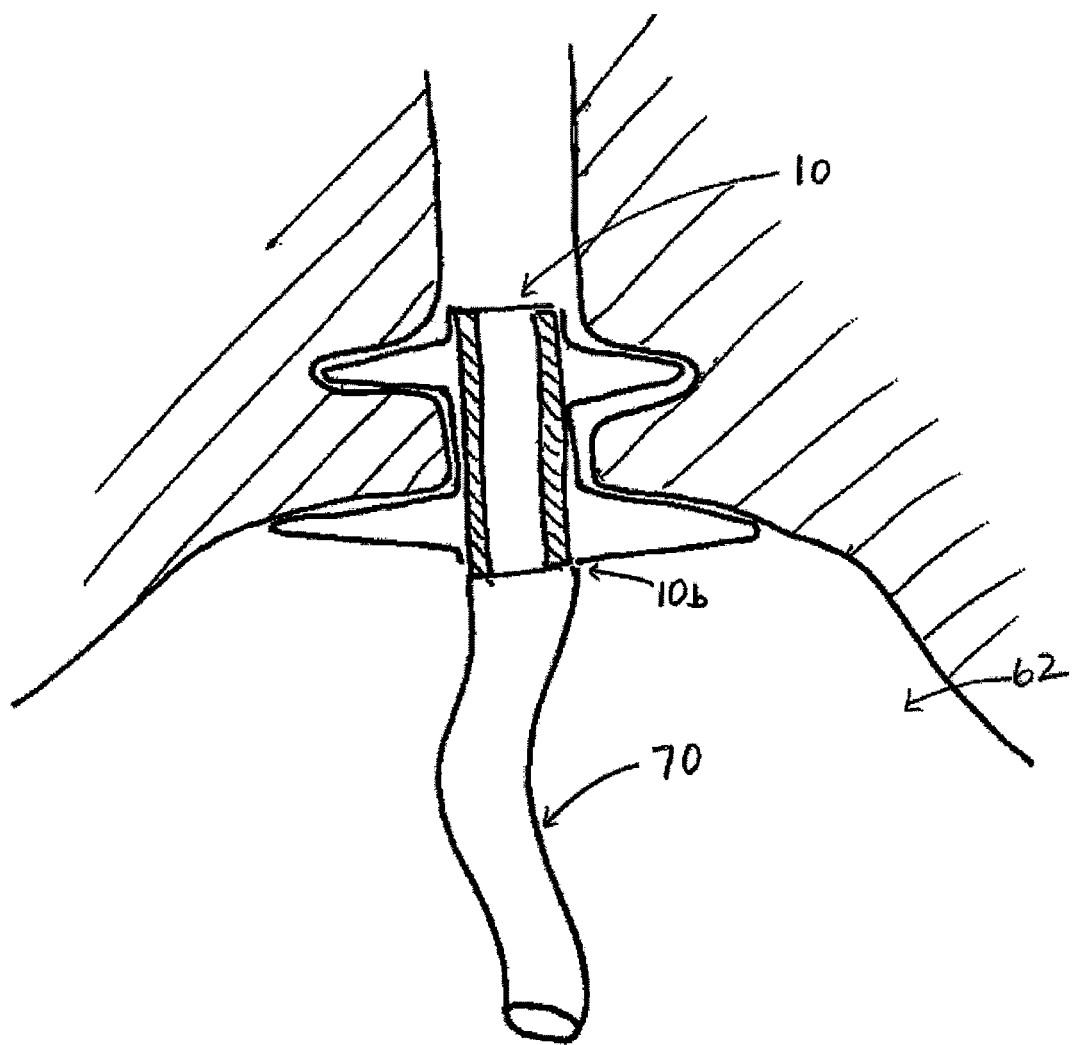
FIG. 36 is a partially cross-sectional view of the anastomotic device of FIG. 35 with a supplemental elongate tubular body disposed therein.

In a gastric narrowing use shown in FIG. 36, a tube 70 can extend from the distal end 10b of the deployed anastomotic device 10 of FIG. 35. In such a case, the pyloric section of the stomach 62 can be held permanently open by the insertion of the device 10, thereby enhancing rapid transit of digested food and reducing absorption. The diameter and length of the tube 70 can vary, but by way of non-limiting example can be about 1 cm in diameter and about 4 cm in length. In another non-limiting example, the diameter can be about 1.6 cm. The volume of the tube 70 can also vary but in one embodiment is in the range of about 10 to 30 mls. The tube 70 can extend between the distal portion 12b of the device 10 and the stomach 62, or can extend in length on either end. For example, the tube 70 can pass through the pylorus or any other small bowel to inhibit local absorption of digested food. The inlet diameter of the device 10 can also be reduced as described above.

Figure 37:
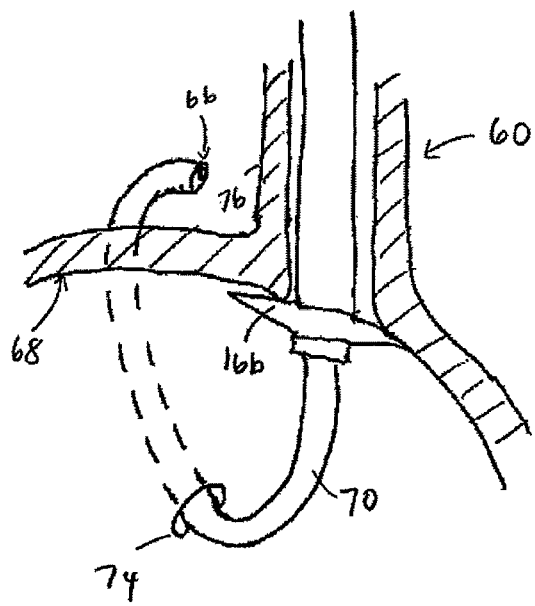
FIG. 37 is a partially cross-sectional view of the anastomotic device and the actuator portion of FIG. 34 with an endoscope advanced through a hole in the stomach.
Figure 38:
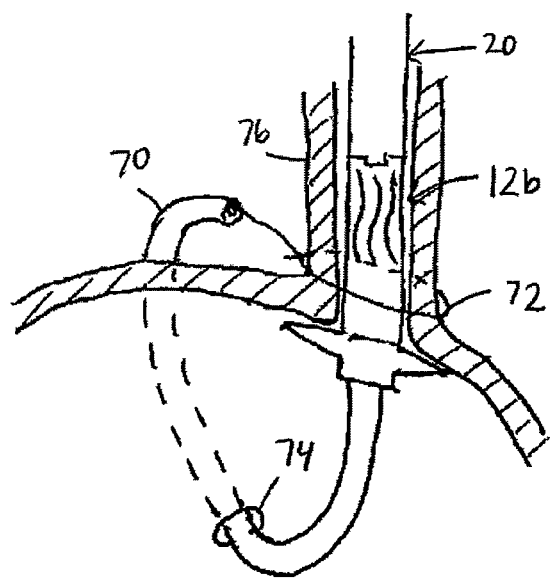
FIG. 38 is a partially cross-sectional view of the anastomotic device and the actuator portion of FIG. 37 with a band fixed around the esophagus.
Figure 39:
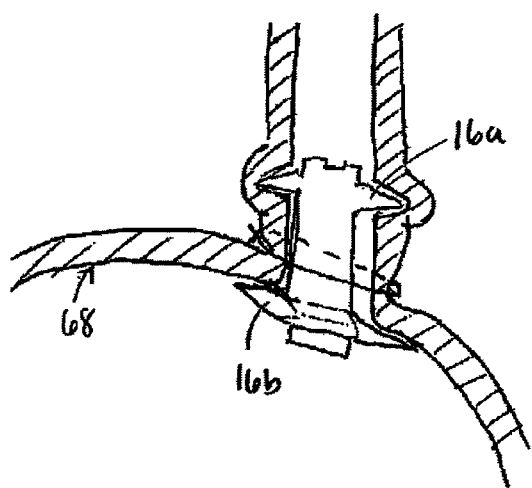
FIG. 39 is a partially cross-sectional view of the anastomotic device of FIG. 38 with the proximal wings deployed.

During gastro-esophageal deployment of the device 10 such as in a gastric reflux use, illustrated in FIGS. 37-39, it may be desirable to fix a band 72 around the esophagus 60 to compress tissue against the non-expanded section (proximal portion 12a) of the outer elongate body 12. The band 72 can include any surgically safe device capable of securing tissue, e.g., a section of suture or a flexible member. The band 72 is typically fixed following deployment of the distal wings 16b and prior to deployment of the proximal wings 16a, but the sequence of events can vary. To fix the band 72, the endoscope 64 can be advanced through a hole 74 in the stomach wall and onward until its end 66 provides a view of an esophageal wall 76, e.g., by being adjacent to the wall 76. Tools can be advanced through the working channel of the endoscope 64 to position the band 72 around the esophagus 60. The band 72 can be tightened around the esophagus 60 to compress the esophageal wall 76 against the outer elongate body 12 positioned within the esophageal lumen as shown in FIG. 38. The endoscope 64 can be withdrawn into the stomach 62, the proximal wings 16a can be deployed, and the actuator 20 can be removed as shown in FIG. 39. Although the proximal and distal portions 12a, 12b are typically in fluid communication, in some embodiments such as in the gastric reflux use, a closure element, such as a solid pin made of surgically safe material, can be disposed in the mid-portion area 13 between the proximal and distal wings 16a, 16b to prevent fluid leakage. The hole 74 in the stomach wall 68 can be repaired using any technique, such as using another embodiment of an anastomotic device 80 illustrated in FIGS. 40-42.

Figure 40:
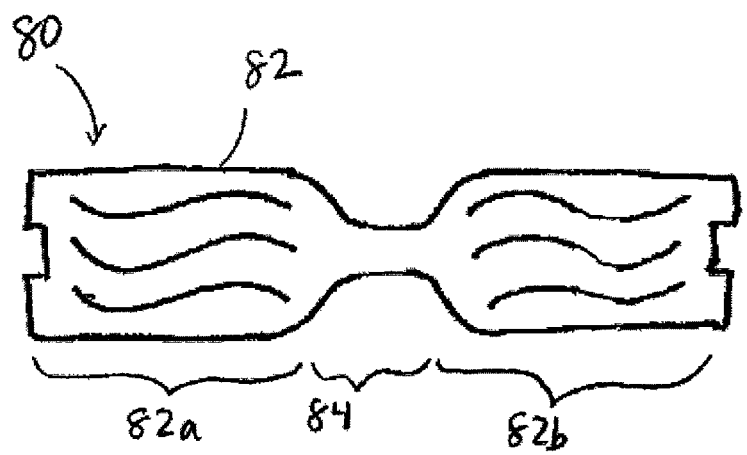
FIG. 40 is a perspective view of another exemplary embodiment of an anastomotic device in an initial, unformed configuration.
Figure 41:
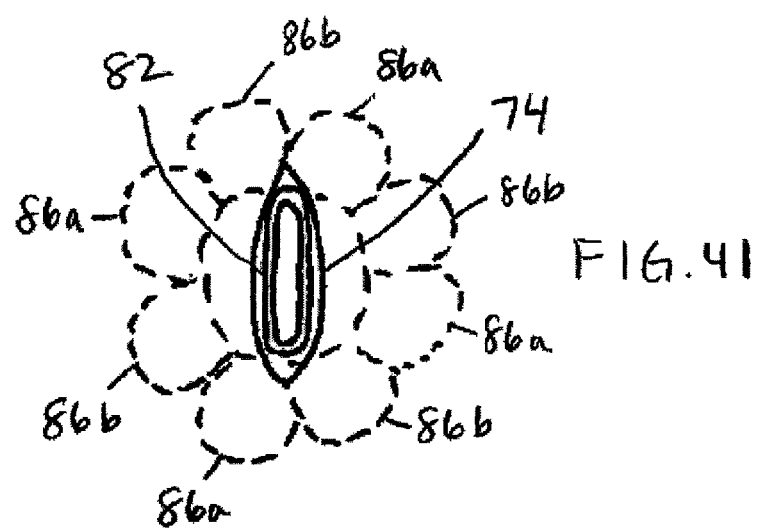
FIG. 41 is a cross-sectional view of the anastomotic device of FIG. 40 deployed in the stomach hole of FIG. 39.

The anastomotic device 80 of FIG. 40 is similar in form and function to the device 10 of FIG. 1 except that a mid-portion 84 of a generally elongate tubular body 82 of the device 80 is reduced in size compared to its proximal and distal portions 82a, 82b. The mid-portion 84 can have any cross-sectional shape, e.g., elliptical (including circular). The proximal and distal portions 82a, 82b can have the same or different cross-sectional shapes as the mid-portion 84, although the proximal and distal portions 82a, 82b typically have the same cross-sectional shape as each other. Once deployed, the mid-portion 84 can be positioned within the hole 74 as shown in FIG. 41, with deployed proximal and distal wings 86a, 86b bearing against the stomach walls on each side.

Figure 42:
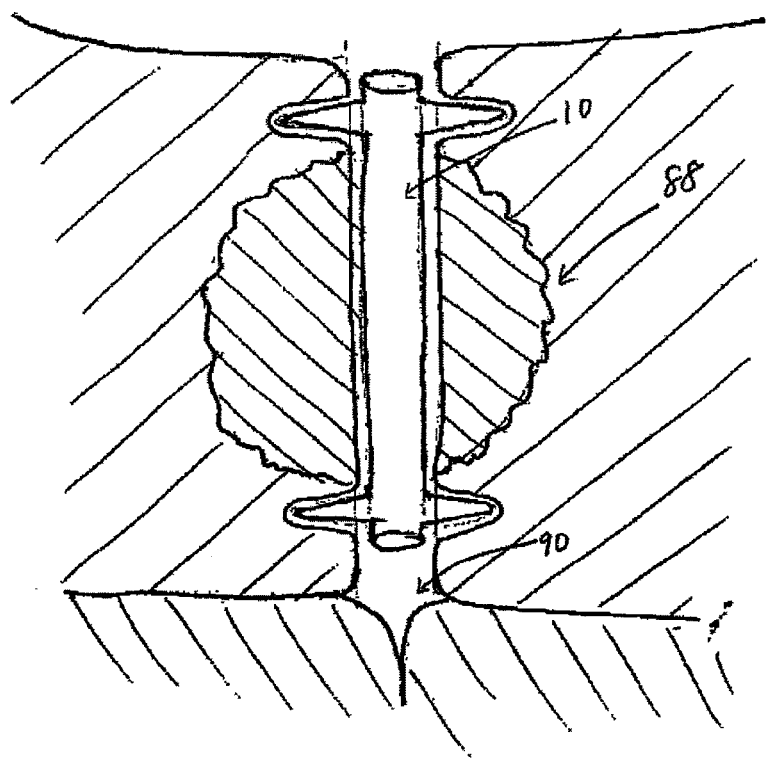
FIG. 42 is a partially cross-sectional view of the anastomotic device of FIG. 1 with its distal and proximal wings deployed around a prostate.
Figure 43:
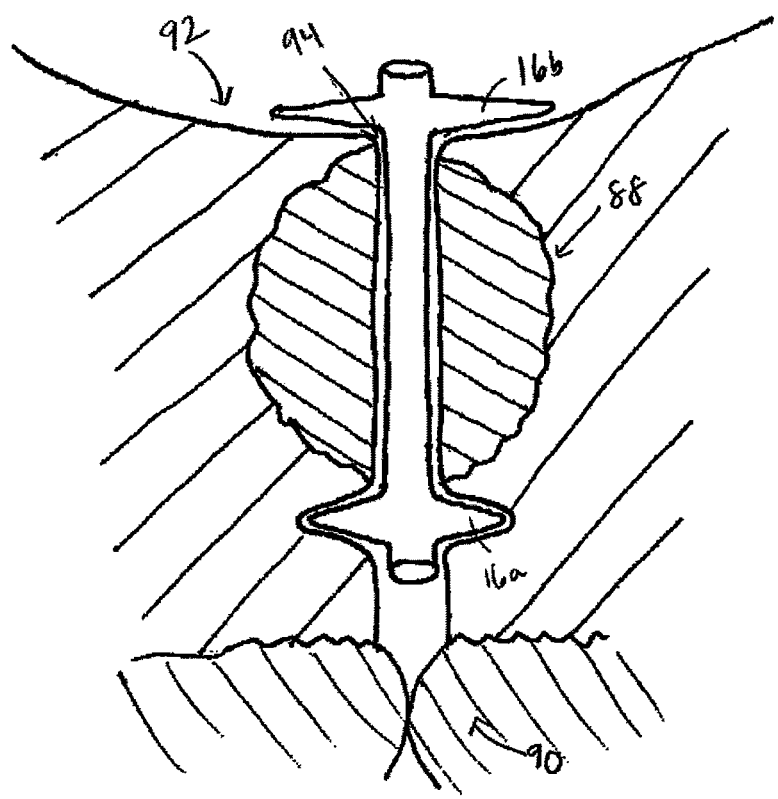
FIG. 43 is another partially cross-sectional view of the anastomotic device of FIG. 1 with its distal and proximal wings deployed around a prostate.

In yet another use, the anastomotic device 10 can be placed across obstructions within the body to recreate a body lumen. One such example is across a prostate 88, as illustrated in FIGS. 42-43. The anastomotic device 10 can be advanced across the prostate 88, and the distal wings 16b can be deployed into tissue. The non-expandable mid-portion 13 can be of sufficient length to cross an obstruction (e.g., the prostate 88) so that the proximal wings 16a can be expanded on the opposite side and not interfere with other parts of the body, e.g., an external sphincter 90. The device 10 can also be deployed across the prostate 88 such that the distal wings 16b are located within a bladder 92, as shown in FIG. 43. Once deployed, the distal wings 16b can be withdrawn against a bladder neck 94. The proximal wings 16a can then be deployed on the other side of the obstruction 88, thereby providing an open conduit between both ends. The deployed distal and proximal wings 16a, 16b generally inhibit migration of the device 10.

Figure 44:
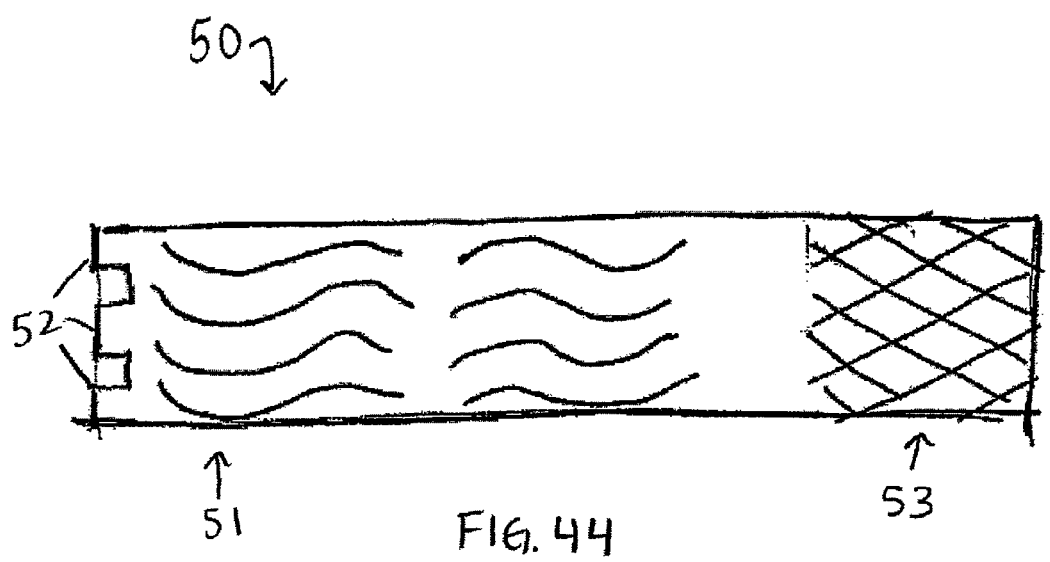
FIG. 44 is a perspective view of still another exemplary embodiment of an anastomotic device in an initial, unformed configuration.

FIG. 44 illustrates another embodiment of an anastomotic device 50, which in an exemplary embodiment is configured for use in endovascular aneurysm repair (EVAR), such as in treating infra-renal aneurysms. The anastomotic device 50 is similar in form and function to the device 10 of FIG. 1 except that, while a proximal end 51 of the device 50 includes tabs 52 (similar to the tabs 15a, 15b described above), a distal end 53 of the device 50 does not include tabs. At least the distal end 53 is formed from a deformable material to allow the distal end 53 to be deformed into a desired configuration. The distal end 53, and optionally the entire device, can also or alternatively be formed from a shape memory material.

Figure 45:
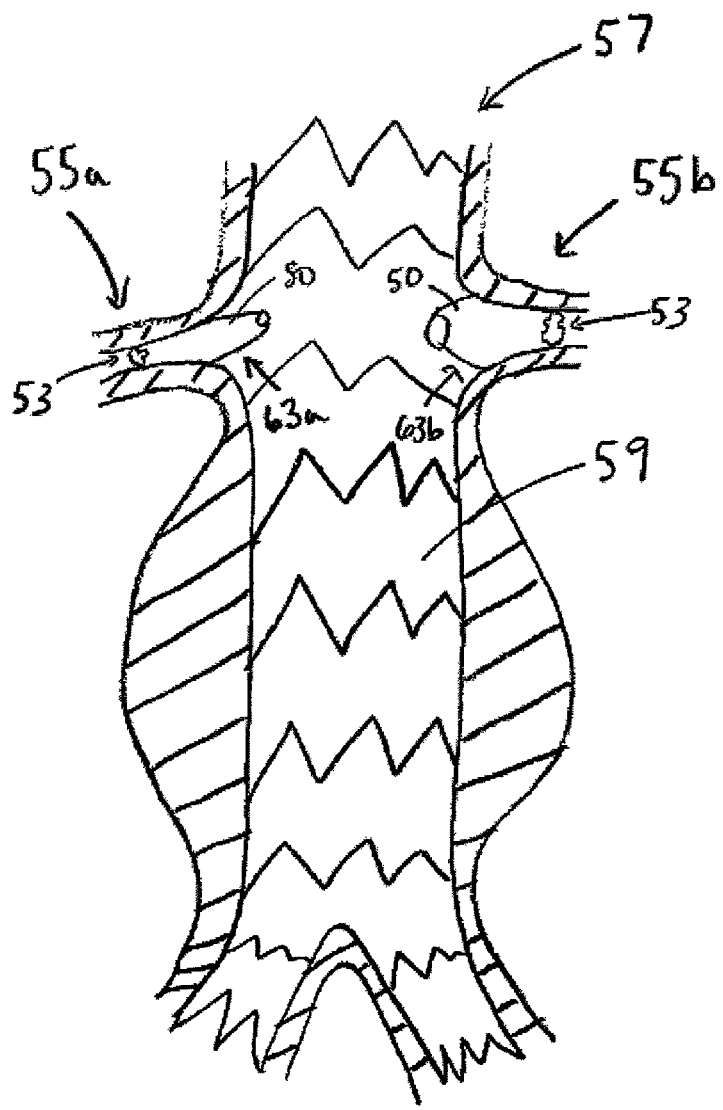
FIG. 45 is a cross-sectional view of the anastomotic device of FIG. 44 deployed in an artery.
Figure 46:
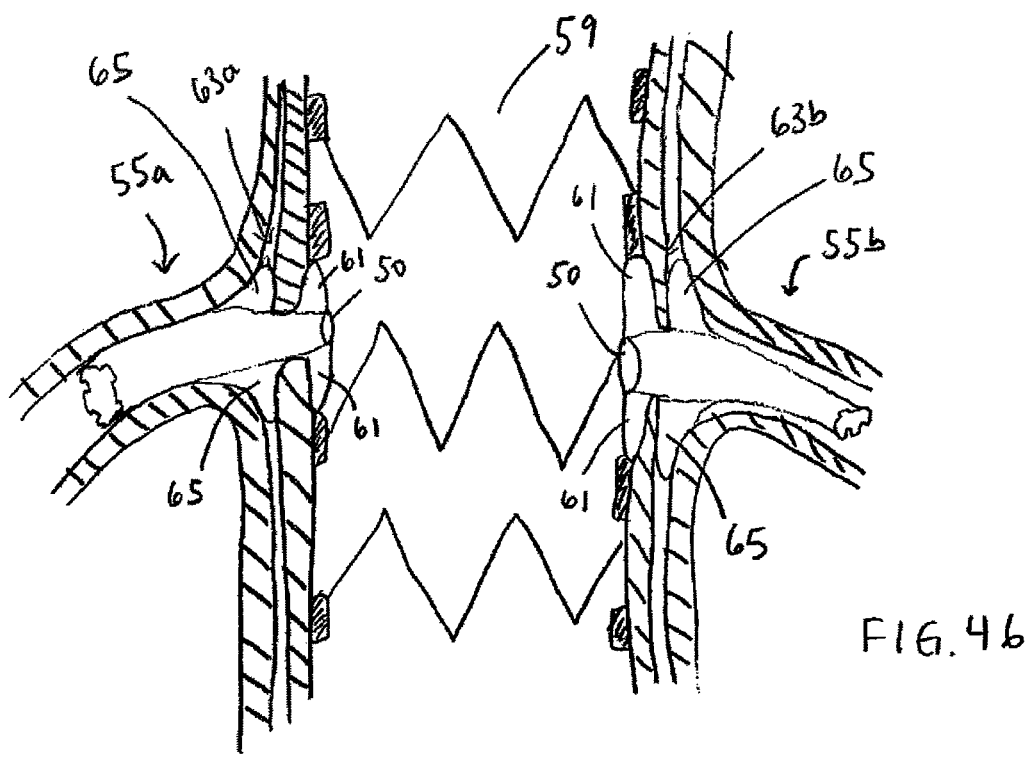
FIG. 46 is a partially cross-sectional view of the anastomotic device of FIG. 45 with its distal and proximal wings deployed.

In one exemplary EVAR procedure, illustrated in FIGS. 45-46, locations of side branch protrusions 55a, 55b of an artery 57 and any other related information (e.g., orientation, length, and diameter of the protrusions 55a, 55b and/or the arterial aneurysm) can be determined. Devices such as guidewires, radiopaque rings, or stents can be inserted into the side branch protrusions 55a, 55b to mark their locations. An aneurysm graft 59 can be inserted and deployed in the artery 57. An instrument such as a curved needle inserted through the graft 59 can be used to puncture through the graft 59 at junctions 63a, 63b between the artery 57 and the side branch protrusions 55a, 55b, and a guidewire can be inserted into each of the side branch protrusions 55a, 55b through the needles, and the needles can be removed. If necessary, one or more devices (e.g., a series of dilators increasing in diameter, a dilator having a screw head at its distal end, a hole punch, an inflatable balloon with blades attached to its surface, wings having cutting edges, etc.) can be advanced over each guidewire to facilitate further expanding of the puncture in the graft 59 at either or both junctions 63a, 63b between the artery 57 and the side branch protrusions 55a, 55b. A person skilled in the art can appreciate that the guidewires can be inserted into either of the side branch protrusions 55a, 55b at any time during the procedure, although they are typically deployed before any devices 50.

A first anastomotic device 50 can be advanced over one of the guidewires extending into one of the side branch protrusions 55a, 55b with the device's distal end 53 leading and extending into one of the side branch protrusions 55a, 55b. As shown in FIG. 46, proximal wings 61 of the device 50 can be deployed inside the lumen of the graft 59, and the proximal wings 61 can be pushed against the wall of the graft 59 at the junctions 63a, 63b. Distal wings 65 can be deployed on the other side of the junction 63a, 63b, thereby anchoring the side branch protrusion 55a, 55b to the graft 57 and sealing the junction 63a, 63b. Following deployment of the wings 61, 65, the distal end 53 can be flared outward to anchor its location within the side branch protrusion 55a, 55b. For example, a balloon catheter can be used to cause the distal end 53 to flare outward. Since the distal end 53 is formed from an deformable material, it will retain its flared shape. If a shape memory material such as nitinol is used to form the device 50, any of the wings 61, 65 and/or the distal end 53 can be heat set into position.

A person skilled in the art will appreciate that the various methods and devices disclosed herein can be formed from a variety of materials. Moreover, particular components can be implantable and in such embodiments the components can be formed from various biocompatible materials known in the art. Exemplary biocompatible materials include, by way of non-limiting example, composite plastic materials, biocompatible metals and alloys such as stainless steel, magnesium alloys, titanium, titanium alloys and cobalt-chromium alloys, and any other material that is biologically compatible and non-toxic to the human body.

One skilled in the art will appreciate further features and advantages based on the above-described embodiments.

Accordingly, the description is not to be limited by what has been particularly shown and described, except as indicated by the appended claims.

What is claimed is:

1. A system for joining tissue, comprising:
   an inner elongate tubular body defining a fluid flow lumen therethrough; and
   an outer elongate tubular body disposed around the inner elongate tubular body and having proximal and distal portions adapted to expand upon rotation to form proximal and distal wings configured to engage tissue therebetween, the inner elongate tubular body having slots formed at proximal and distal portions thereof that are configured to engage with corresponding protrusions formed on an inner sidewall of the proximal and distal portions of the outer elongate tubular body to fixedly maintain the proximal and distal wings in an expanded position.

2. The system of claim 1, wherein the outer elongate tubular body includes a plurality of slits formed in each of the proximal and distal portions and configured to allow the proximal and distal portions to expand to form the proximal and distal wings.

3. The system of claim 2, wherein the slits extend longitudinally along the outer elongate tubular body in a proximal-distal direction, and wherein the slits are spaced axially around the outer elongate tubular body.

4. The system of claim 2, wherein slits in the distal portion of the outer elongate tubular body have a greater length than slits in the proximal portion of the outer elongate tubular body.

5. The system of claim 2, wherein the plurality of slits are curved and asymmetrical such that a curve on a first portion of each slit is greater in length than a curve on a second portion of each slit.

6. The system of claim 1, further comprising an actuator removably coupled to the inner elongate tubular body and adapted to slide and rotate to expand the proximal and distal portions of the outer elongate tubular body.

7. A system for joining tissue, comprising:
   an outer elongate tubular body having proximal and distal portions with a plurality of slits formed therein, the proximal and distal portions being movable from an unexpanded configuration to an expanded configuration in which the proximal and distal portions form proximal and distal wings that are configured to engage tissue therebetween; and
   an inner elongate tubular body disposed within the outer elongate tubular body and having an outer diameter that is smaller than an inner diameter of the outer elongate tubular body, the inner elongate tubular body having first mating features that are formed at different longitudinal positions along a length of each of proximal and distal portions of the inner elongate tubular body and that are configured to selectively mate with corresponding second mating features formed at the proximal and distal portions of the outer elongate tubular body to fixedly maintain the proximal and distal wings in the expanded configuration.

8. The system of claim 7, wherein the inner elongate tubular body has a length that is less than a length of the outer elongate tubular body when the outer elongate tubular body is in the unexpanded configuration.

9. The system of claim 7, wherein slits in the distal portion of the outer elongate tubular body have a greater length than slits in the proximal portion of the outer elongate tubular body.

10. The system of claim 7, wherein the plurality of slits are curved and asymmetrical such that a curve on a first portion of each slit is greater in length than a curve on a second portion of each slit.

11. A system for joining tissue, comprising:
    an outer elongate tubular body having proximal and distal portions that are expandable to form proximal and distal wings configured to engage tissue therebetween, at least one of the proximal and distal portions of the outer elongate tubular body including first mating features formed at different longitudinal positions along a length thereof; and
    an inner elongate tubular body having an outer diameter that is smaller than an inner diameter of the outer elongate tubular body, the inner elongate tubular body being disposed within the outer elongate tubular body and having open proximal and distal ends that are positioned adjacent to open proximal and distal ends, respectively, of the outer elongate tubular body when the proximal and distal wings are in an expanded configuration, wherein at least one of the proximal and distal portions of the inner elongate tubular body includes second mating features formed at different longitudinal positions along a length thereof, and wherein each second mating feature is configured to engage one of the first mating features such that a distance between the proximal and distal wings in the expanded configuration is adjustable.

12. The system of claim 11, wherein the inner elongate tubular body has a length that is less than a length of the outer elongate tubular body prior to forming the proximal and distal wings.

13. The system of claim 11, wherein the proximal and distal portions of the outer elongate tubular body include a plurality of slits formed therein for facilitating formation of the proximal and distal wings.

14. The system of claim 13, wherein slits in the distal portion have a greater length than slits in the proximal portion.

15. The system of claim 13, wherein the plurality of slits are curved and asymmetrical such that a curve on a first portion of each slit is greater in length than a curve on a second portion of each slit.

* * * * *